(12) United States Patent
Nelson et al.

(10) Patent No.: US 8,994,934 B1
(45) Date of Patent: Mar. 31, 2015

(54) SYSTEM AND METHOD FOR EYE SAFE DETECTION OF UNKNOWN TARGETS

(75) Inventors: Matthew Nelson, Harrison City, PA (US); Patrick Treado, Pittsburgh, PA (US); Robert Schweitzer, Pittsburgh, PA (US); Robert D'Agostino, Conway, AR (US)

(73) Assignee: ChemImage Corporation, Pittsburgh, PA (US)

( * ) Notice: Subject to any disclaimer, the term of this patent is extended or adjusted under 35 U.S.C. 154(b) by 503 days.

(21) Appl. No.: 13/373,333

(22) Filed: Nov. 10, 2011

Related U.S. Application Data

(60) Provisional application No. 61/456,662, filed on Nov. 10, 2010.

(51) Int. Cl.
*G01N 21/00* (2006.01)
*G01N 33/00* (2006.01)
*G01J 3/02* (2006.01)

(52) U.S. Cl.
CPC .............. *G01N 33/0057* (2013.01); *G01J 3/02* (2013.01)
USPC .......................................................... 356/73

(58) Field of Classification Search
CPC .......... G01J 3/36; G01J 3/44; G01N 33/0057; G01N 21/65
See application file for complete search history.

(56) References Cited

U.S. PATENT DOCUMENTS

| | | | |
|---|---|---|---|
| 3,398,294 A | 8/1968 | Eberhard | |
| 4,560,275 A | 12/1985 | Goetz | |
| 5,196,682 A | 3/1993 | Englehardt | |
| 5,216,484 A | 6/1993 | Chao et al. | |
| 5,394,237 A | 2/1995 | Chang | |
| 5,615,673 A * | 4/1997 | Berger et al. | 600/326 |
| 6,006,140 A | 12/1999 | Carter | |

(Continued)

FOREIGN PATENT DOCUMENTS

| | | |
|---|---|---|
| EP | 17646438 | 1/2007 |
| EP | 1902301 | 3/2008 |

(Continued)

OTHER PUBLICATIONS

Sharma, et al, "Stand-Off Raman Spectroscopic Detection of Minerals on Planetary Surfaces", Hawaii Institute of Geophysics and Planetology, pp. 2391-2407, 2003.

(Continued)

*Primary Examiner* — Tri T Ton
*Assistant Examiner* — Willie Merrell, II
(74) *Attorney, Agent, or Firm* — Pepper Hamilton LLP

(57) ABSTRACT

The present disclosure provides for a system and method for detecting and identifying unknown targets. At least one region of interest comprising an unknown target in a sample scene may be targeted using SWIR spectroscopic techniques. A region of interest may be surveyed to thereby determine whether or not a human is present. This surveying may be achieved my assessing LWIR data, data acquired from motion sensors, and combinations thereof. If no human is present in a region of interest, the region may be interrogated using Raman spectroscopic techniques to thereby obtain a Raman data set representative of the region of interest. This Raman data set may be assessed to thereby identify said unknown target. This assessment may be achieved by comparing the Raman data set to a reference data sets in a reference database, where each reference data set is associated with a known target.

22 Claims, 27 Drawing Sheets

(56) References Cited

U.S. PATENT DOCUMENTS

| | | | |
|---|---|---|---|
| 6,025,603 A * | 2/2000 | Hasegawa et al. | 250/556 |
| 6,244,535 B1 | 6/2001 | Felix | |
| 6,274,871 B1 | 8/2001 | Dukor et al. | |
| 6,422,508 B1 | 7/2002 | Barnes | |
| 6,477,907 B1 | 11/2002 | Chambers | |
| 6,606,566 B1 | 8/2003 | Sunshine | |
| 6,621,574 B1 * | 9/2003 | Forney et al. | 356/301 |
| 6,658,915 B2 | 12/2003 | Sunshibne | |
| 6,820,012 B2 | 11/2004 | Sunshine | |
| 6,822,742 B1 | 11/2004 | Kalayeh | |
| 6,844,817 B2 | 1/2005 | Gleine | |
| 6,967,612 B1 | 11/2005 | Gorman | |
| 6,985,216 B2 | 1/2006 | Treado | |
| 6,985,233 B2 | 1/2006 | Tuschel | |
| 6,995,371 B2 | 2/2006 | Garber | |
| 6,995,846 B2 | 2/2006 | Kalayeh | |
| 7,012,695 B2 | 3/2006 | Maier | |
| 7,084,972 B2 | 8/2006 | Treado | |
| 7,088,435 B2 | 8/2006 | Brestel et al. | |
| 7,164,117 B2 | 1/2007 | Breed | |
| 7,193,210 B2 | 3/2007 | Garber | |
| 7,239,974 B2 | 7/2007 | Gulati | |
| 7,246,613 B1 | 7/2007 | Mohar | |
| 7,262,839 B2 | 8/2007 | Treado | |
| 7,277,178 B2 | 10/2007 | Shpantzer | |
| 7,286,222 B2 | 10/2007 | Gardner | |
| 7,295,308 B1 | 11/2007 | Samuels | |
| 7,307,705 B2 | 12/2007 | Treado | |
| 7,322,267 B1 | 1/2008 | Munson | |
| 7,386,372 B2 | 6/2008 | Breed | |
| 7,417,727 B2 | 8/2008 | Polonskiy | |
| 7,420,664 B2 | 9/2008 | Treado et al. | |
| 7,420,675 B2 | 9/2008 | Giakos | |
| 7,440,096 B2 | 10/2008 | Gardner | |
| 7,486,395 B2 | 2/2009 | Treado | |
| 7,502,118 B2 | 3/2009 | Shpantzer | |
| 7,511,624 B2 | 3/2009 | Shaw | |
| 7,525,102 B1 | 4/2009 | Henshaw | |
| 7,541,588 B2 | 6/2009 | Tabirain | |
| 7,542,138 B2 | 6/2009 | Gardner | |
| 7,548,310 B2 | 6/2009 | Gardner | |
| 7,551,715 B2 | 6/2009 | Rothschild | |
| 7,573,570 B2 | 8/2009 | Zhang | |
| 7,596,242 B2 | 9/2009 | Breed | |
| 7,644,606 B2 | 1/2010 | Sheen | |
| 7,663,502 B2 | 2/2010 | Breed | |
| 7,676,062 B2 | 3/2010 | Breed | |
| 7,687,276 B2 | 3/2010 | Kunz | |
| 7,692,775 B2 | 4/2010 | Treado et al. | |
| 8,379,193 B2 | 2/2013 | Gardner | |
| 2001/0052979 A1 | 12/2001 | Treado et al. | |
| 2003/0058112 A1 | 3/2003 | Gleine | |
| 2003/0123056 A1 | 7/2003 | Barnes | |
| 2003/0216869 A1 | 11/2003 | Sunshine | |
| 2004/0051867 A1 | 3/2004 | Brestel | |
| 2004/0191859 A1 | 9/2004 | Tabacco | |
| 2004/0253759 A1 | 12/2004 | Garber | |
| 2005/0030533 A1 | 2/2005 | Treado | |
| 2005/0030545 A1 | 2/2005 | Tuschel | |
| 2005/0030657 A1 | 2/2005 | Maier | |
| 2005/0041244 A1 | 2/2005 | Treado | |
| 2005/0079626 A1 | 4/2005 | Kunz | |
| 2005/0105099 A1 | 5/2005 | Shpantzer | |
| 2005/0134859 A1 | 6/2005 | Kalayeh | |
| 2005/0264813 A1 | 12/2005 | Giakos | |
| 2006/0007437 A1 | 1/2006 | Treado | |
| 2006/0021498 A1 | 2/2006 | Moroz | |
| 2006/0022139 A1 | 2/2006 | Garber | |
| 2006/0146315 A1 | 7/2006 | Treado | |
| 2006/0167595 A1 | 7/2006 | Breed et al. | |
| 2006/0170922 A1 | 8/2006 | Wang et al. | |
| 2006/0203238 A1 | 9/2006 | Gardner, Jr. et al. | |
| 2006/0208169 A1 | 9/2006 | Breed et al. | |
| 2006/0209301 A1 | 9/2006 | Gardner | |
| 2006/0254522 A1 | 11/2006 | Shaw | |
| 2006/0256330 A1 | 11/2006 | Leipertz | |
| 2006/0262304 A1 | 11/2006 | Carron | |
| 2006/0268266 A1 | 11/2006 | Gardner | |
| 2007/0007384 A1 | 1/2007 | Sliwa | |
| 2007/0081156 A1 | 4/2007 | Treado | |
| 2007/0086624 A1 | 4/2007 | Breed | |
| 2007/0098142 A1 | 5/2007 | Rothschild | |
| 2007/0118324 A1 | 5/2007 | Gulati | |
| 2007/0125951 A1 | 6/2007 | Snider | |
| 2007/0127030 A1 | 6/2007 | Shpantzer | |
| 2007/0153268 A1 | 7/2007 | Panza et al. | |
| 2007/0163431 A1 | 7/2007 | Mohar | |
| 2007/0216898 A1 | 9/2007 | Gardner | |
| 2007/0221849 A1 | 9/2007 | Tabirian | |
| 2007/0262574 A1 | 11/2007 | Breed | |
| 2007/0268485 A1 | 11/2007 | Polonskiy | |
| 2007/0282506 A1 | 12/2007 | Breed | |
| 2008/0036580 A1 | 2/2008 | Breed | |
| 2008/0036593 A1 | 2/2008 | Rose-Pehrsson | |
| 2008/0051957 A1 | 2/2008 | Breed | |
| 2008/0084560 A1 | 4/2008 | Zhang | |
| 2008/0088837 A1 | 4/2008 | Gardner | |
| 2008/0129581 A1 | 6/2008 | Douglass | |
| 2008/0144885 A1 | 6/2008 | Zucherman | |
| 2008/0154535 A1 | 6/2008 | Sparks | |
| 2008/0157940 A1 | 7/2008 | Breed | |
| 2008/0159591 A1 * | 7/2008 | Ruedin | 382/103 |
| 2008/0165344 A1 | 7/2008 | Treado | |
| 2008/0180675 A1 | 7/2008 | Sheen | |
| 2008/0191137 A1 | 8/2008 | Poteet | |
| 2008/0198365 A1 | 8/2008 | Treado | |
| 2008/0204757 A1 | 8/2008 | Manning | |
| 2008/0236275 A1 | 10/2008 | Breed | |
| 2008/0258071 A1 | 10/2008 | Arnold | |
| 2008/0268548 A1 | 10/2008 | Zuckerman | |
| 2008/0295783 A1 | 12/2008 | Furton | |
| 2009/0046538 A1 | 2/2009 | Breed | |
| 2009/0092284 A1 | 4/2009 | Breed | |
| 2009/0095885 A1 | 4/2009 | Hager | |
| 2009/0101843 A1 | 4/2009 | Henshaw | |
| 2009/0128802 A1 | 5/2009 | Treado et al. | |
| 2009/0202128 A1 | 8/2009 | Gorian et al. | |
| 2009/0236528 A1 | 9/2009 | Shpantzer | |
| 2009/0252650 A1 | 10/2009 | Lakshmanan | |
| 2009/0257555 A1 | 10/2009 | Chalmers | |
| 2010/0044570 A1 * | 2/2010 | McGill et al. | 250/338.5 |
| 2010/0225899 A1 | 9/2010 | Treado | |
| 2010/0240140 A1 * | 9/2010 | Fine et al. | 436/147 |
| 2011/0033082 A1 | 2/2011 | Beckstead | |
| 2011/0080577 A1 | 4/2011 | Nelson | |
| 2011/0085164 A1 | 4/2011 | Nelson | |
| 2011/0089323 A1 | 4/2011 | Treado | |

FOREIGN PATENT DOCUMENTS

| | | |
|---|---|---|
| EP | 2083259 | 7/2009 |
| WO | WO/91/08466 | 6/1991 |
| WO | WO/01/33212 | 5/2001 |
| WO | WO0140896 | 6/2001 |
| WO | WO/03/059735 | 7/2003 |
| WO | WO/03/102534 | 11/2003 |
| WO | WO/2005/006198 | 1/2005 |
| WO | WO2005001900 | 1/2005 |
| WO | WO/2005008200 | 1/2005 |
| WO | WO/2005/010474 | 3/2005 |
| WO | WO/2007/001379 | 1/2007 |
| WO | WO/2007/011391 | 1/2007 |
| WO | WO/2007/013000 | 2/2007 |
| WO | WO/2007/032814 | 3/2007 |
| WO | WO/2007/044067 | 4/2007 |
| WO | WO/2007/044593 | 4/2007 |
| WO | WO/2007/051092 | 5/2007 |
| WO | WO/2007/056753 | 5/2007 |
| WO | WO/2007/064099 | 7/2007 |
| WO | WO/2007/101297 | 9/2007 |
| WO | WO/2007/120996 | 10/2007 |
| WO | PCT/US06/22647 | 11/2007 |
| WO | WO/2007/103897 | 11/2007 |
| WO | WO/2007/123555 | 11/2007 |

(56) References Cited

FOREIGN PATENT DOCUMENTS

| WO | WO/2007/010832 | 1/2008 |
| --- | --- | --- |
| WO | WO/2008/002659 | 1/2008 |
| WO | WO/2008/048979 | 4/2008 |
| WO | WO/2008/024344 | 6/2008 |
| WO | WO/2008/097262 | 8/2008 |
| WO | WO/2008/105812 | 9/2008 |
| WO | WO/2008/140473 | 11/2008 |
| WO | WO2009019689 | 2/2009 |
| WO | WO2009154765 | 12/2009 |
| WO | WO2010108086 | 9/2010 |

OTHER PUBLICATIONS

Sharma, et al, Portable Stand-off Raman and Mie-Rayleigh LIDAR for Cloud, Aerosols, and Chemical Monitoring, Proceedings of SPIE vol. 5154, LIDAR Remote Sensing for Environmental Monitoring IV, pp. 1-14, 2003.

Sharma, et al., Remote Pulsed Laser Raman Spectroscopy System for Mineral Analysis on Planetary Surfaces to 66 Meters, Applied Spectroscopy, vol. 56, No. 6, 2002, pp. 699-705.

PCT/US06/22647, Notification of Transmittal of the International Search Report and the Written Opinion of the International Searching Authority, Mar. 31, 2008.

Gardner, C. et al, "Remote Chemical Biological and Explosive Agent Detection Using a Robot-Based Raman Detector", SPIE Defense + Security, Proc. SPIE 6962, 69620T (2003).

Pati, B. et al., "Passively Q-switched Nd:YLF laser in a D-rod configuration," in Conference on Lasers and Electro-Optics, OSA Technical Digest (Optical Society of America, Washington, DC 2008), paper CFJ5.

Fuller, M. et al., "High gain end pumped lasers," OSA TOPS, vol. 19, Advanced Solid State Lasers, Walter Bosenberg and Martin M. Feijer (eds), 1998, Optical Society of America.

Kyusho, Y et al., "High-energy subnanosecond compact laser syster with diode-pumped, Q-switched Nd YVO4 laser," OSA TOPS on Advanced Solid State Lasers, vol. 1, Stephen A. Payne and Clifford Pollock (eds), 1996, Optical Society of America.

Zheng, S. et al, "Laser-diode end-pumped passively Q-switched laser with Cr4+:YAG saturable absorber," Opt. Engineering, vol. 41, #9, 2002, pp. 2271-2275.

Nelson et al, "Single-Shot Multiwavelength Imaging of Laser Plumes," Applied Spectroscopy, vol. 52, No. 2, Feb. 1, 1998.

Extended European Search Report, PCT/US2006022647, Aug. 10, 2010.

* cited by examiner

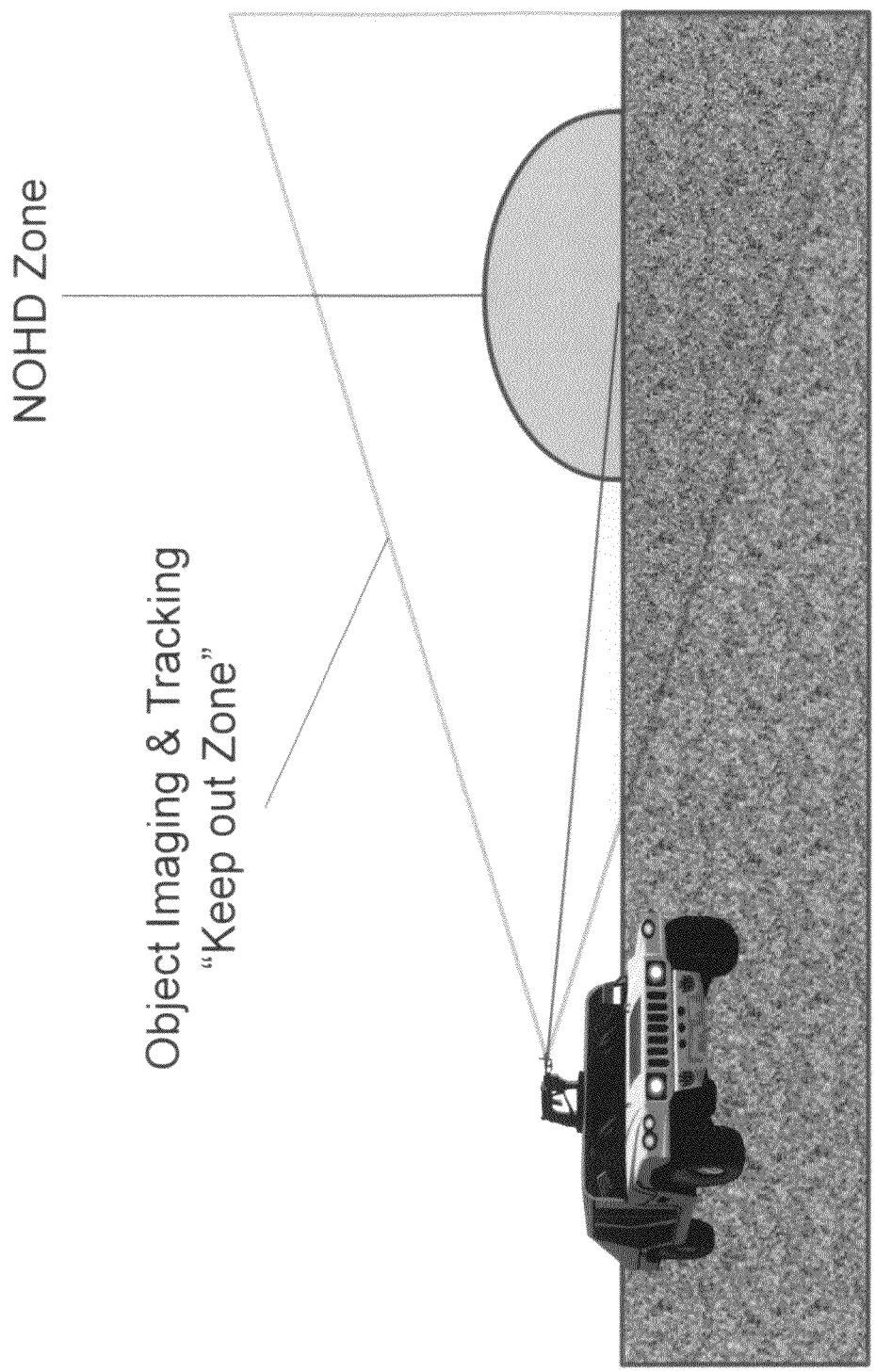

SWIR Subsystem
210b

Raman Subsystem
210a

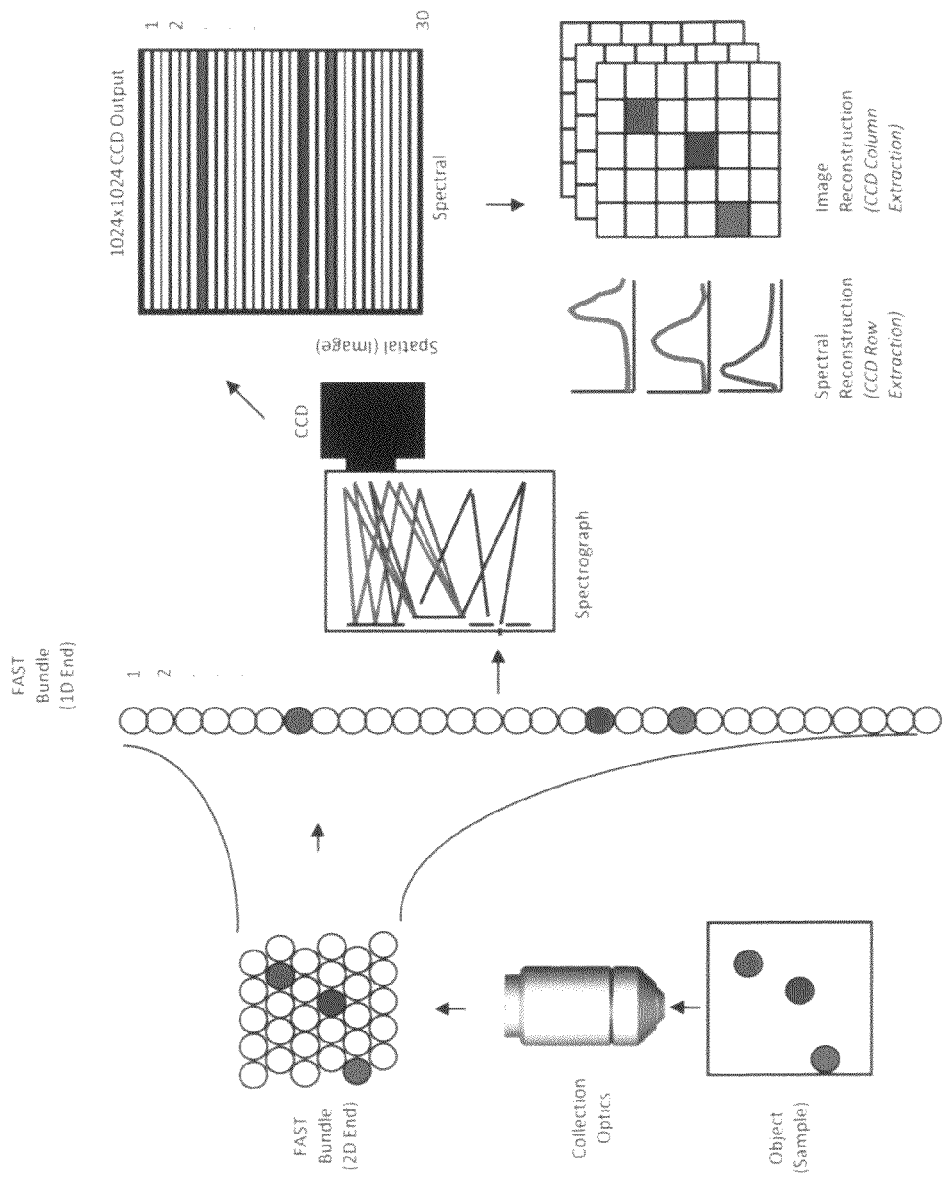
FIG. 5A
FIG. 5B

600

610: targeting at least one region of interest in a sample scene, wherein targeting comprises generating and analyzing a SWIR data set

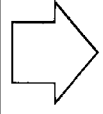

620: surveying said region of interest, wherein surveying comprises generating and analyzing a LWIR data set to determine whether or not a human is present

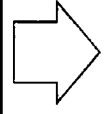

630: if no human presence is detected, identifying said unknown target, wherein identifying comprises generating an analyzing a Raman data set

FIG. 6

SYSTEM AND METHOD FOR EYE SAFE DETECTION OF UNKNOWN TARGETS

RELATED APPLICATIONS

This Application claims priority under 35 U.S.C. §119(e) to U.S. Provisional Patent Application No. 61/456,662, filed on Nov. 10, 2010, entitled "Eye-Safer Standoff Raman Hyperspectral Imaging Detection of Threats." This Application is hereby incorporated by reference in its entirety.

GOVERNMENT LICENSE RIGHTS

This invention was made with government support under Contract No. W911NF-09-C-0078 awarded by U.S. Army RDECOM. The government has certain rights in the invention.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger targets, in the range of millimeter to meter dimensions, macro lens optics are appropriate. For samples located within relatively inaccessible environments, flexible fiberscope or rigid borescopes can be employed. For very large scale targets, such as planetary targets, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the entire area encompassing the sample simultaneously using an electronically tunable optical imaging filter such as an acousto-optic tunable filter (AOTF) or a LCTF. This may be referred to as "wide-field imaging". Here, the organic material in such optical filters are actively aligned by applied voltages to produce the desired bandpass and transmission function. The spectra obtained for each pixel of such an image thereby forms a complex data set referred to as a hyperspectral image (HSI) which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR), long wave infrared (LWIR) wavelengths and to some overlapping ranges. These correspond to wavelengths of about 180-380 nm (UV), 380-700 nm (VIS), 700-2500 nm (NIR), 850-1800 nm (SWIR), 2500-25000 nm (MIR), and 7500-13500 nm (LWIR).

Proliferation of chemical, biological, and explosive (CBE) threats is a growing danger to civilian and military personnel. There exists a need for sensor systems that can rapidly detect these CBE threats at a standoff distance. Examples of technologies that hold potential for such detection include short wave infrared (SWIR) spectroscopy and Raman spectroscopy.

Raman spectroscopy requires probing a sample with a laser beam. The issue of laser safety must be solved before widespread deployment is possible. There exists a need to develop strategies to eliminate the laser hazard to both operators and bystanders.

SUMMARY OF THE INVENTION

The present disclosure relates generally to a system and method for assessing unknown targets. More specifically, the present disclosure provides for a system and method for detecting and identifying unknown targets using SWIR and Raman spectroscopic techniques. Areas of interest, likely to comprise CBE threats, may be targeted during wide area surveillance of a sample scene using SWIR techniques. This disclosure provides for local confirmation of these potential threats using standoff detection via a Raman-ST sensor. This disclosure also provides for systems and methods that are eye-safe, enabled by surveying an area using motion detectors and LWIR data.

Hyperspectral sensors hold potential for the detection of CBE threats. The present disclosure provides for a Raman standoff (Raman-ST) sensor which may incorporate fiber array spectral translator (FAST) hyperspectral imaging technology. A FAST device provides for collecting Raman scattered photons from a scene through a telescope and project them onto the two dimensional end of a FAST bundle that is drawn into a one dimensional, distal array coupled to an imaging spectrograph. Software may then extract the full spectral/spatial information, which is embedded in a single CCD image frame. The acquired spatial-specific Raman information allows threat materials to be computationally differentiated within a complex mixture of background materials.

The system and method disclosed herein hold potential for the detection of explosive and other threats. Raman hyperspectral technology holds potential for the standoff detection of explosives and provides for: highly selective detection, spatially-independent sampling benefits, and eye-safe. LWIR detection and human object imaging and tracking algorithms, used in conjunction with Raman HSI provides a higher degree of eye-safety. The present disclosure also contemplates that mid wave infrared (MWIR) may be used either alone or in conjunction with another spectroscopic technique such as Raman, SWIR, LWIR, visible, and combinations thereof.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings:

FIGS. 1A and 1B are illustrative of exemplary operational configurations of a system and method of the present disclosure.

FIG. 5A is illustrative of FAST technology.

FIG. 5B is representative of an exemplary packaging option of a FAST device.

FIG. 6 is representative of a method of the present disclosure.

DETAILED DESCRIPTION

Reference will now be made in detail to the embodiments of the present disclosure, examples of which are illustrated in the accompanying drawings. Wherever possible, the same reference numbers will be used throughout the drawings to refer to the same or like parts.

Figure 1B:
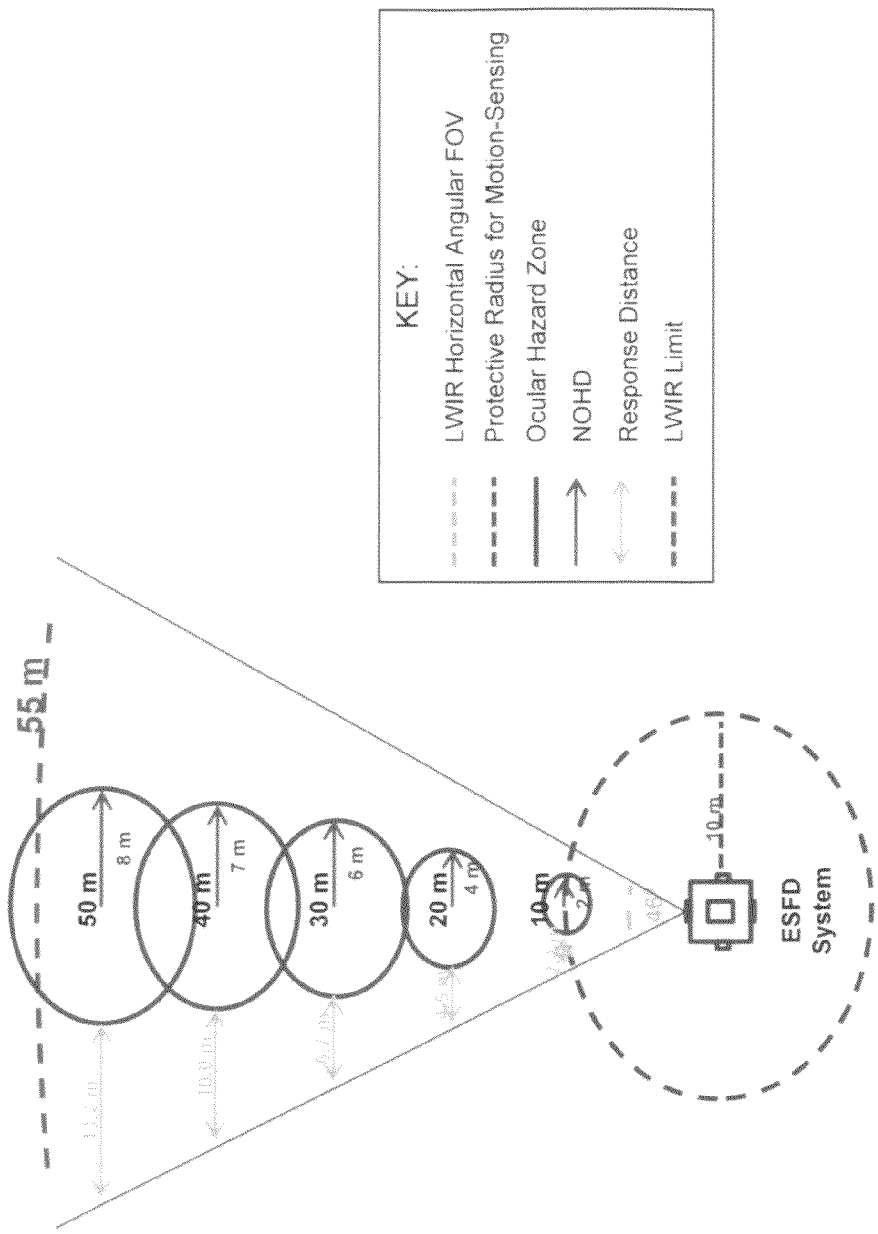

The present disclosure provides for a standoff system for detecting and identifying unknown targets. Examples of operational configurations are illustrated by FIGS. 1A-1B. In one embodiment, the system and method of the present disclosure may be configured to provide for SWIR wide area surveillance of sample scenes. This surveillance may direct the pointing of a Raman sensor by identifying areas of interest comprising potential threats. The present disclosure contemplates a Nominal Ocular Hazard Distance (NOHD) zone protection with human object imaging and a tracking laser kill switch. Specifically, FIG. 1A is illustrative of one CONOPS configuration and FIG. 1B is illustrative of an operational configuration of the present disclosure.

Figures 2A, 2B:
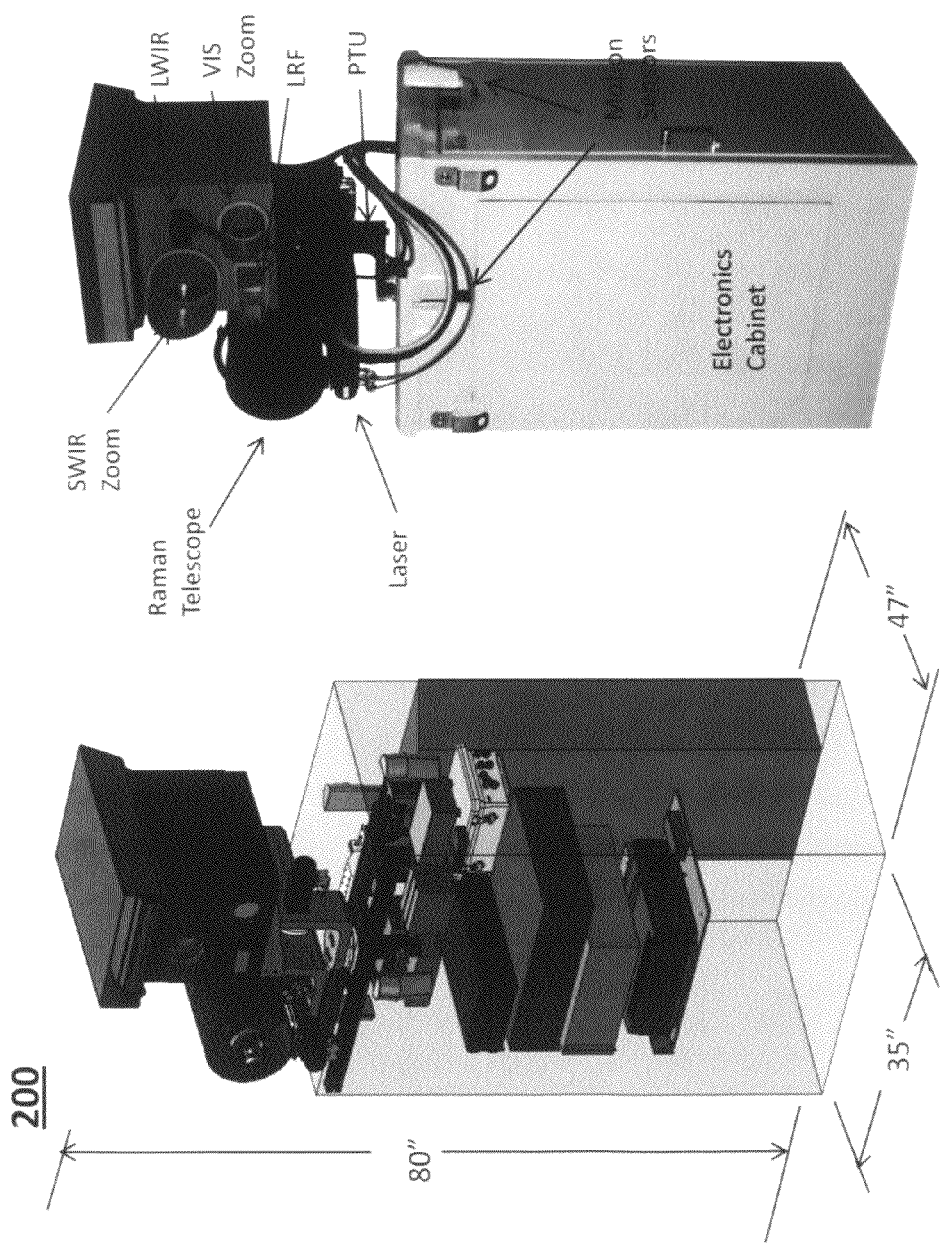
FIGS. 2A and 2B are representative of exemplary packaging options of a system of the present disclosure.
Figure 2D:
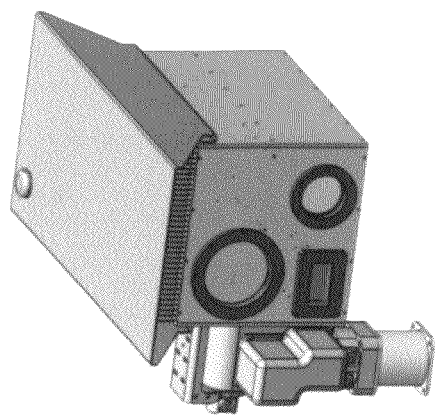
FIGS. 2C and 2D are representative of exemplary packaging options of subsystems of a system of the present disclosure.
Figure 2C:
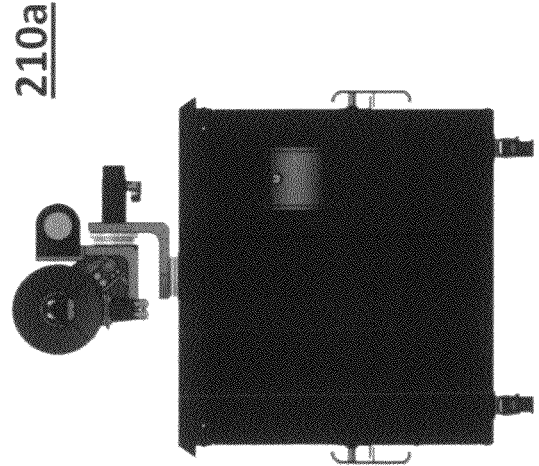

The present disclosure provides for a method for detecting, tracking, and identifying unknown targets. Exemplary housing configurations of a system 200 of the present disclosure are illustrated in FIGS. 2A and 2B. Exemplary configurations of a Raman subsystem 210a and a SWIR subsystem 210b are illustrated in FIGS. 2C and 2D.

Figure 3A:
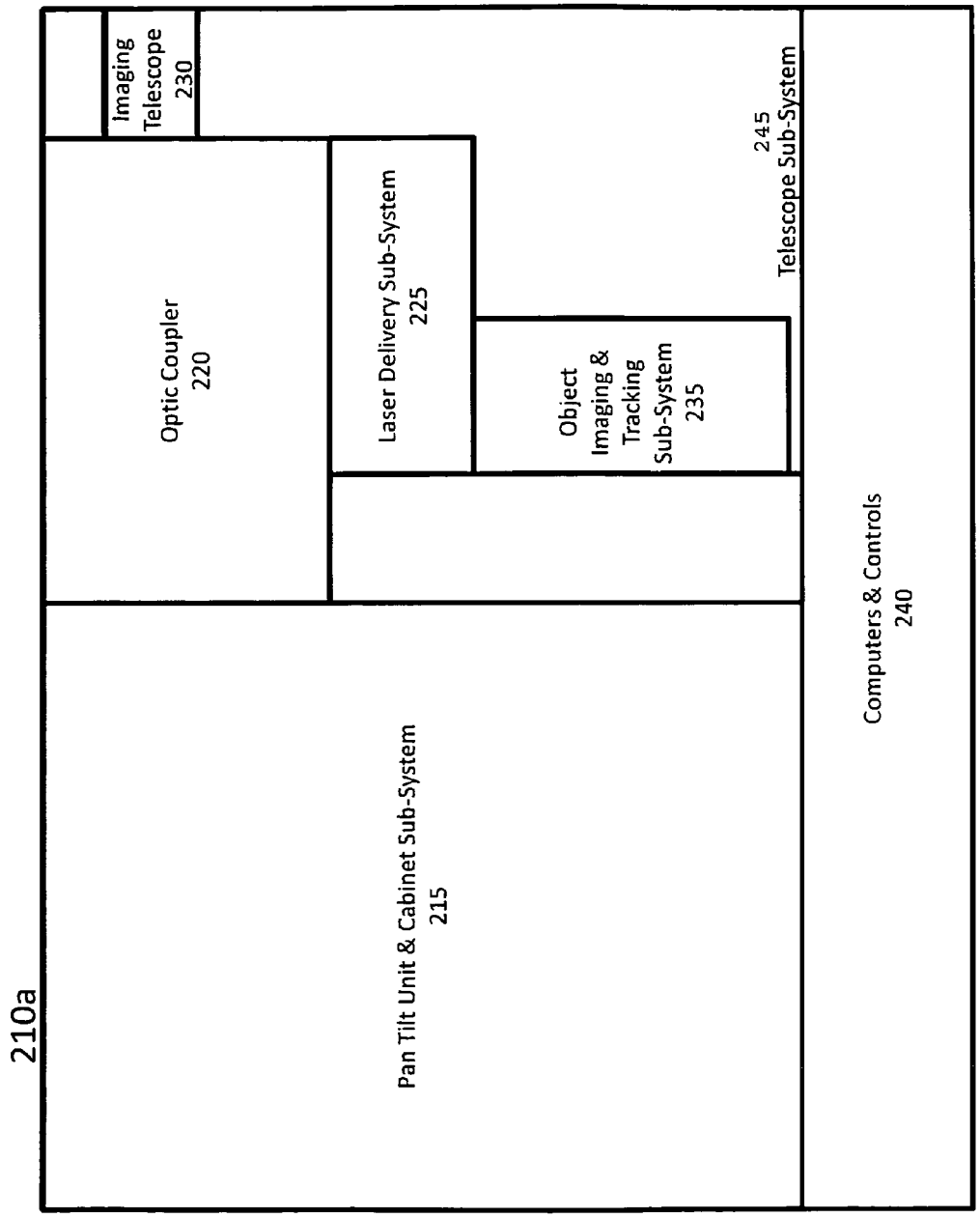
FIG. 3A is representative of a subsystem of a system of the present disclosure.
Figure 3B:
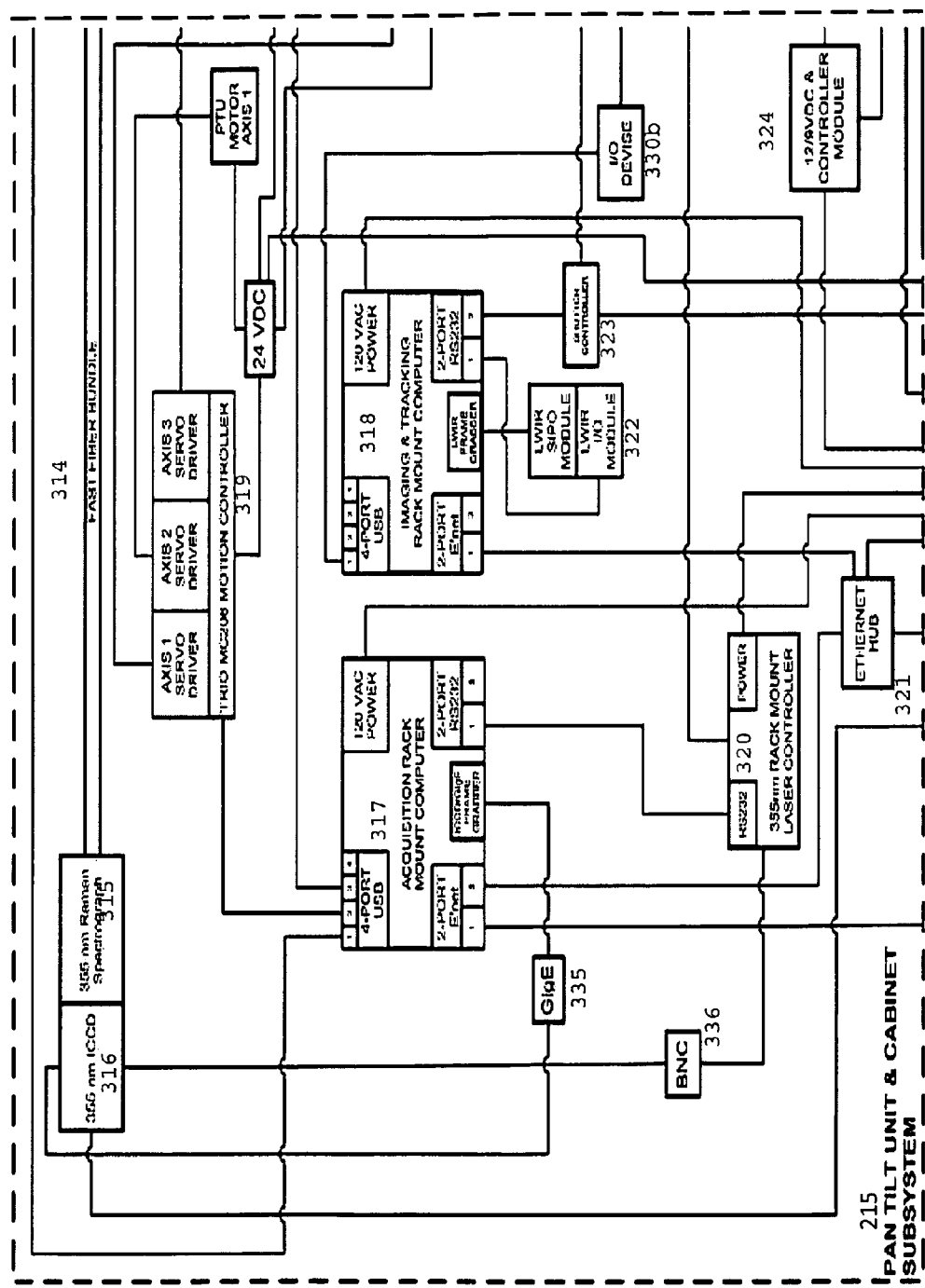
FIG. 3B is representative of a subsystem of a system of the present disclosure.
Figure 3C:
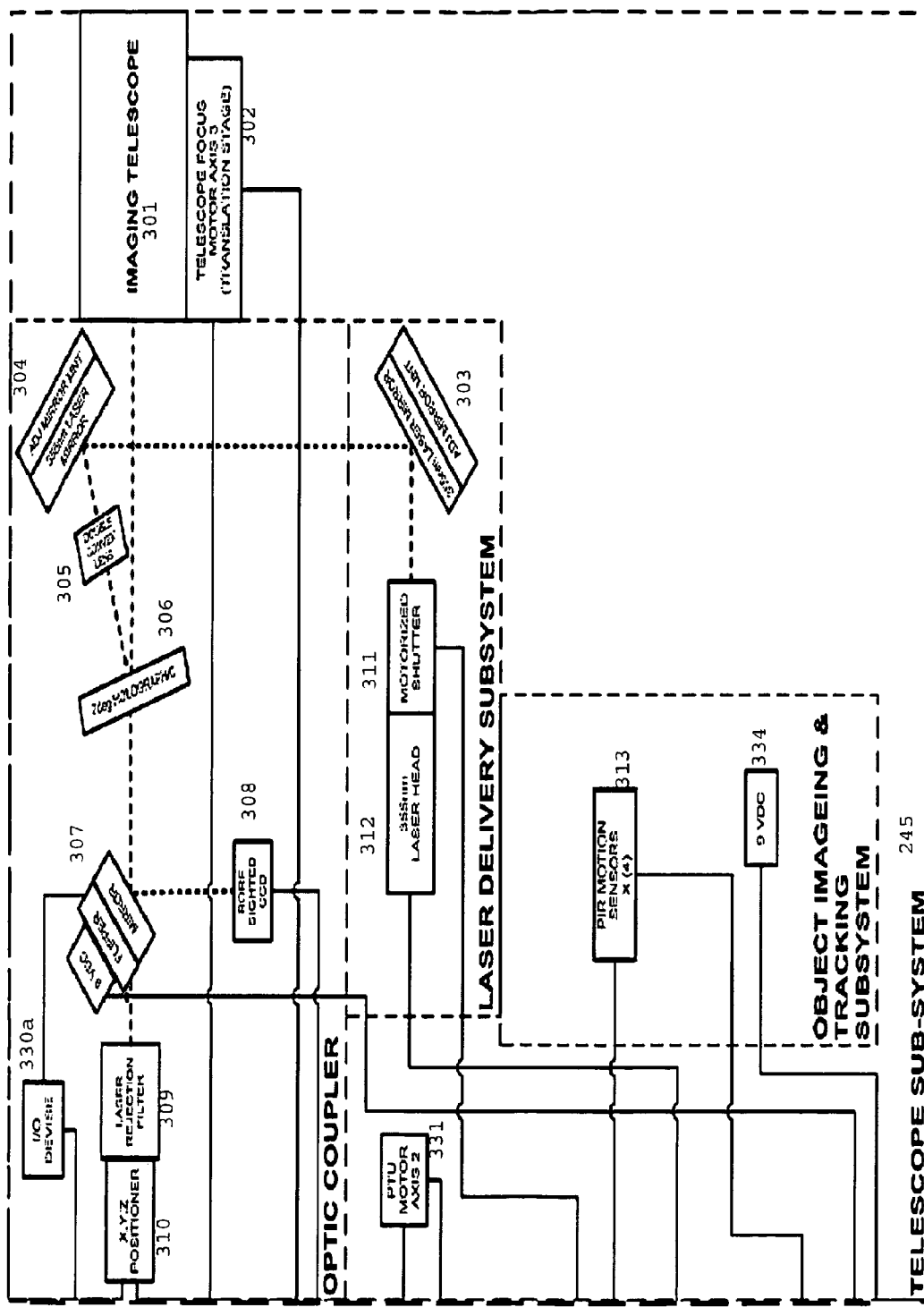
FIG. 3C is representative of a subsystem of a system of the present disclosure.

FIGS. 3A-3C are provided as illustrative embodiments of the subsystems of system 200. FIG. 3A is representative of the Raman subsystem 210a. As an overview, the subsystem 201a may comprise a pan tilt unit (PTU) and cabinet subsystem 215, a telescope subsystem 245, a laser delivery subsystem 225, an optic coupler 220, an object imaging and tracking subsystem 235, and power and system processing components 240. The subsystem 201a may further comprise a telescope subsystem 245.

FIG. 3C is illustrative of a telescope subsystem 245. A telescope subsystem may comprise an imaging telescope 301 and a telescope focus 302. A laser delivery subsystem may comprise a laser head 312 a motorized shutter 311 and mirrors 303. In FIG. 3, laser head 312 is illustrated as comprising a 355 nm laser. The motorized shutter 311 may be configured so as to effectively stop the illumining photons from a laser head 312 from illuminating an unknown target.

Illuminating photons may be directed by mirrors 303 to an optic coupler. This optic coupler may comprise mirrors 304, lens 305, and a holographic filter 306 to direct illuminating photons to an imaging telescope 301. These illumination photons may illuminate a region of interest and thereby generate a plurality of interacted photons. These interacted photons may pass through the device and directed by mirror 307 to either a boresighted CCD 308 and/or through a laser rejection filter 309, x,y,z positioned 310 and to a FAST device 314. FAST device and FAST fiber bundle may be used interchangeably herein. The FAST device may be housed in the pan tilt unit and cabinet subsystem 215, illustrated in FIG. 3B.

FAST technology is illustrated in FIG. 5A. FIG. 5B illustrates an exemplary housing configuration of a FAST device. The FAST system can provide faster real-time analysis for rapid detection, classification, identification, and visualization of, for example, explosive materials, hazardous agents, biological warfare agents, chemical warfare agents, and pathogenic microorganisms, as well as non-threatening targets, elements, and compounds. FAST technology can acquire a few to thousands of full spectral range, spatially resolved spectra simultaneously, This may be done by focusing a spectroscopic image onto a two-dimensional array of optical fibers that are drawn into a one-dimensional distal array with, for example, serpentine ordering. The one-dimensional fiber stack is coupled to an imaging spectrograph. Software may be used to extract the spectral/spatial information that is embedded in a single CCD image frame.

One of the fundamental advantages of this method over other spectroscopic methods is speed of analysis. A complete spectroscopic imaging data set can be acquired in the amount of time it takes to generate a single spectrum from a given material. FAST can be implemented with multiple detectors. Color-coded FAST spectroscopic images can be superimposed on other high-spatial resolution gray-scale images to provide significant insight into the morphology and chemistry of the sample.

The FAST system allows for massively parallel acquisition of full-spectral images. A FAST fiber bundle may feed optical information from is two-dimensional non-linear imaging end (which can be in any non-linear configuration, e.g., circular, square, rectangular, etc.) to its one-dimensional linear distal end. The distal end feeds the optical information into associated detector rows. The detector may be a CCD detector having a fixed number of rows with each row having a predetermined number of pixels. For example, in a 1024-width square detector, there will be 1024 pixels (related to, for example, 1024 spectral wavelengths) per each of the 1024 rows.

The construction of the FAST array requires knowledge of the position of each fiber at both the imaging end and the distal end of the array. Each fiber collects light from a fixed position in the two-dimensional array (imaging end) and transmits this light onto a fixed position on the detector (through that fiber's distal end).

Each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

In one embodiment, the system 200 may comprise FAST technology available from ChemImage Corporation, Pittsburgh, Pa. This technology is more fully described in the following U.S. Patents and Published Patent Applications, hereby incorporated by reference in their entireties: U.S. Pat. No. 7,764,371, filed on Feb. 15, 2007, entitled "System And Method For Super Resolution Of A Sample In A Fiber Array Spectral Translator System"; U.S. Pat. No. 7,440,096, filed on Mar. 3, 2006, entitled "Method And Apparatus For Compact Spectrometer For Fiber Array Spectral Translator"; U.S. Pat. No. 7,474,395, filed on Feb. 13, 2007, entitled "System And Method For Image Reconstruction In A Fiber Array Spectral Translator System"; and U.S. Pat. No. 7,480,033, filed on Feb. 9, 2006, entitled "System And Method For The Deposition, Detection And Identification Of Threat Agents Using A Fiber Array Spectral Translator". In one embodiment, the system 200 may comprise FAST technology wherein a fiber stack comprises at least two columns of fibers spatially offset in parallel. This technology is more fully described in U.S. Patent Application Publication No. 2010/0265502, filed on Apr. 13, 2010, entitled "Spatially And Spectrally Parallelized Fiber Array Spectral Translator System And Method Of Use," which is hereby incorporated by reference in its entirety.

Referring again to FIG. 3B, interacted photons may be transferred via a FAST device 314 to a Raman spectrometer 315 and detector to thereby generate at least one Raman data set. In FIG. 3, this detector is illustrated as a ICCD 316.

The PTC and Cabinet subsystem 215 of subsystem 210a may further comprise various computers and controls 317, 318, 320, 321, 324, a motion controller 319, and a PTU motor axis 331 configured for operating the subsystem 210a. An LWIR module 322 may be configured to generate and assess LWIR data to thereby determine human presence in a scene/region of interest. The LWIR module 322 may be operatively coupled to a shutter controller 323 to control operation of at least one of: a laser head 312 and motorized shutter 311. I/O devices 330a, 330b and BNC 336 and GigE 335 connections and power sources 332, 333a, 333b, and 334 may also be configured to provide additional power and control.

The subsystem 210a may further comprise an object imaging and tracking subsystem. This object imaging and tracking subsystem may comprise one or more motion sensors 313.

Figure 3D:
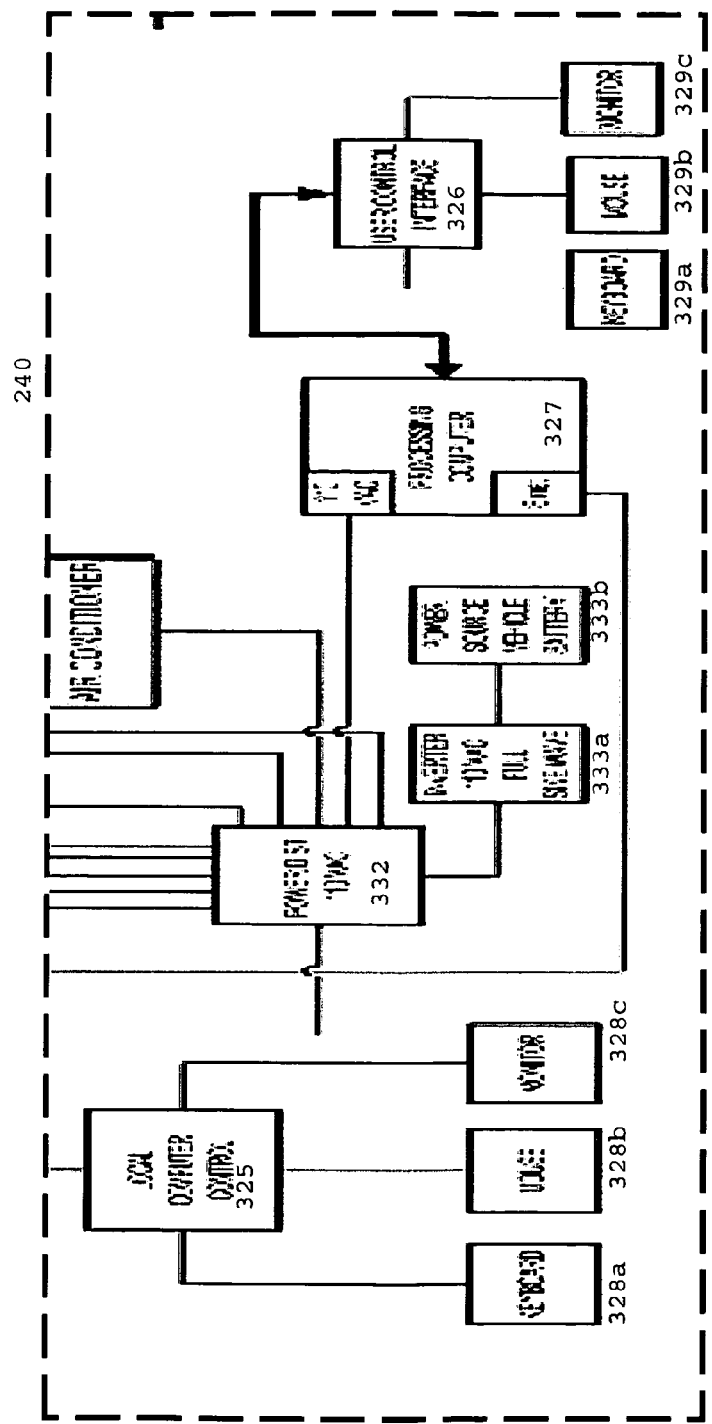
FIG. 3D is representative of a subsystem of a system of the present disclosure.

The subsystem 210a may further comprise various components operatively coupled to subsystems to provide control and power sources to the subsystem and its components 240, illustrated in FIG. 3D. These may include a local computer control 325, a user control interface 326, and processing computer 327. Keyboards 328a and 329a, mouse 328b and 329b, and monitors 328c and 329c.

Components configured for powering the subsystem 332, 333a, 333b, may also be operatively coupled to the subsystem.

Figure 4:
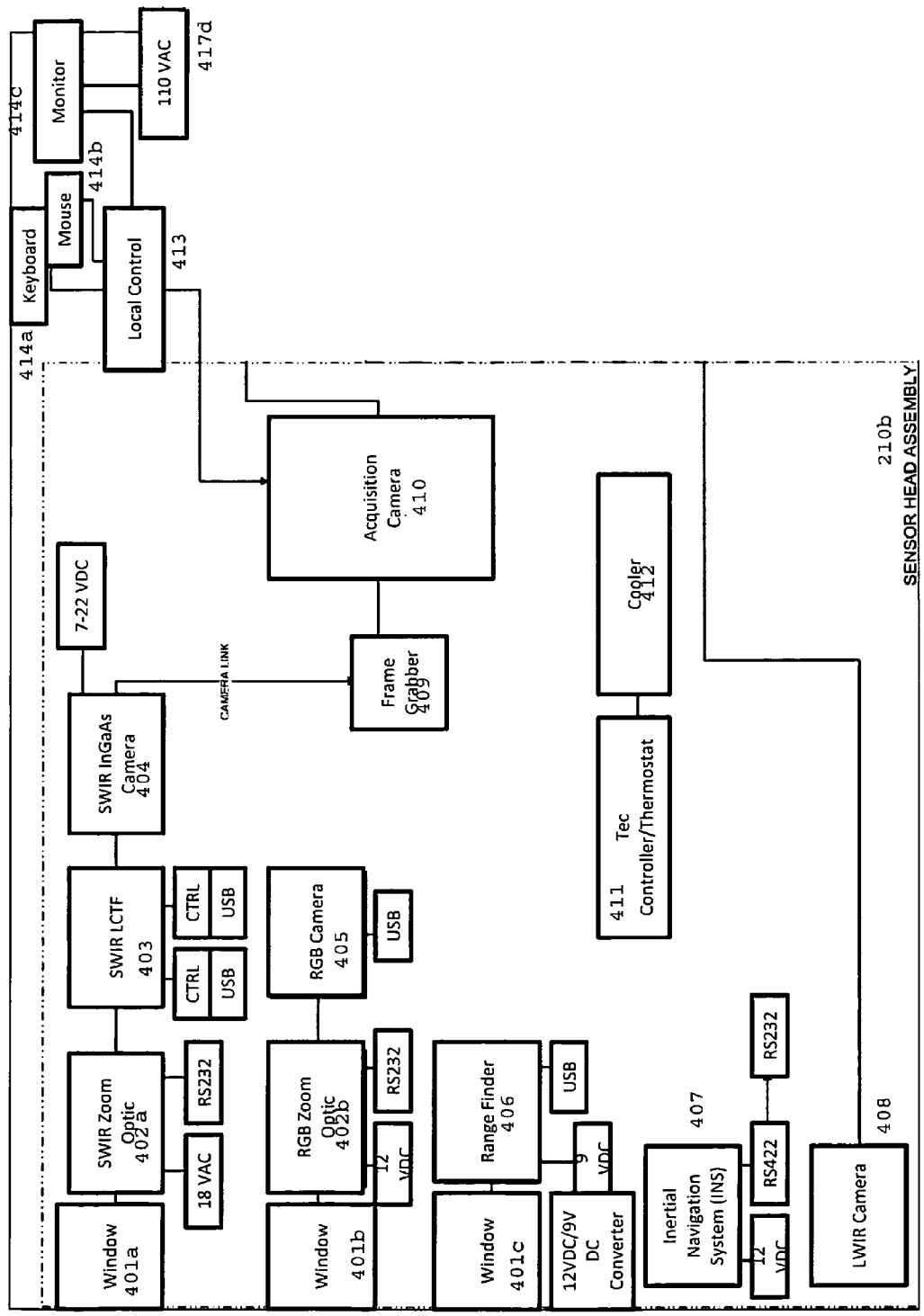
FIG. 4 is representative of a subsystem of a system of the present disclosure.

FIG. 4 is representative of the SWIR subsystem 210b. The subsystem 210b may comprise a sensor head assembly. A sensor head assembly may comprise one or more windows 401a, 401b, and 401c, which may also be referred to as collection lenses, lenses, or collection optics herein. The system may comprise a one or more zoom optics. In one embodiment, a SWIR zoom optic 402a may be operatively coupled to a tunable filter. In FIG. 3, the tunable filter is illustrated as a SWIR liquid crystal tunable filter 403. In another embodiment, the filter may comprise a SWIR multi-conjugate liquid crystal tunable filter. The SWIR liquid crystal tunable filter may 403 may be configured to effectively separate a plurality of interacted photons into a plurality of predetermined wavelength bands. The plurality of interacted photons may be detected by a SWIR detector, illustrated as a SWIR InGaAs Camera 404. However, other embodiments may comprise other detectors known in the art including but not limited to a CCD, an ICCD, an InSb detector, a MCT detector and combinations thereof. In one embodiment is SWIR camera 404 may be operatively coupled to a frame grabber 409.

The sensor head assembly may further comprise a visible zoom optic, illustrated as a RGB zoom optic 402b. This RGB zoom optic 402b may be operatively coupled to visible detector. The visible detector in FIG. 4 is illustrated as an RGB camera 405. However, this visible detector may also comprise a video capture device.

The sensor head assembly of subsystem 210b may further comprise a range finder 406. In one embodiment, at least one of a frame grabber 409, a range finder 406, and an inertial navigation system 407 may be operatively coupled to an acquisition computer 410. This acquisition computer 410 may further, in one embodiment, be coupled to at least one of: a local control 413 and elements housed in a PTU and cabinet subsystem. This PTU cabinet and subsystem may comprise a Ethernet 415 and a processing computer 416. In one embodiment, a local control 413 may comprise at least one of: a keyboard 414a, a mouse 414b, and a monitor 414c. The processing computer 416 may be operatively coupled to a user control interface control 418a. The user control interface system 418a may comprise at least one of: a mouse 418a, keyboard 418b, and monitor 418c.

In one embodiment, the subsystem 210b of the present disclosure may incorporate a high pixel resolution, high frame rate color video camera system to assist in locating targets of interest. The SWIR HSI portion of the system may consist of an InGaAs focal plane camera coupled to a wavelength-agile Multi-Conjugate Filter (MCF) in combination with a zoom optic capable of viewing a large area, or imaging a localized area at high magnification. In one embodiment of operation, an area would first be screened using the wide field setting on the zoom lens. Once the area is screened and potential targets are identified, confirmation of the area may be accomplished as necessary by using the narrow field setting on the zoom lens.

FIG. 6 is representative of a method of the present disclosure. In one embodiment, the method 600 may comprise targeting at least one region of interest in a sample scene in step 610. In one embodiment, a region of interest comprises an unknown target and said targeting may be achieved using SWIR spectroscopic techniques. Targeting may further comprise generating at least one SWIR data set representative of said region of interest and analyzing said SWIR data set to thereby identify one or more regions of interest. In one embodiment, at least one SWIR data set may be obtained at a predetermined wavelength wherein this predetermined wavelength is material specific. In one embodiment, said SWIR data set comprises at least one of: a SWIR spectrum, a spatially accurate wavelength resolved SWIR image, and combinations thereof. In one embodiment, said SWIR data set comprises a hyperspectral SWIR image.

In step 620 a region of interest may be surveyed to determine whether or not a human is present. In one embodiment, this surveying may be achieved my generating and analyzing at least one LWIR data set representative of a region of interest. In one embodiment, said LWIR data set comprises at least one of: a LWIR spectrum, a LWIR image, and combinations thereof. In one embodiment, said LWIR data set comprises a hyperspectral LWIR image.

In one embodiment, surveying a region of interest may further comprise applying at least one of an object detection algorithm, an object tracking algorithm, and combinations thereof. In one embodiment, the present disclosure provides for object detection. This may include application of motion detection techniques to find moving objects. Adaptive threshold algorithms may be used to vary detection thresholds with the content of a scene. ROIs positions and geometric and/or statistical properties may be extracted and fed into a tracker.

Figure 8:
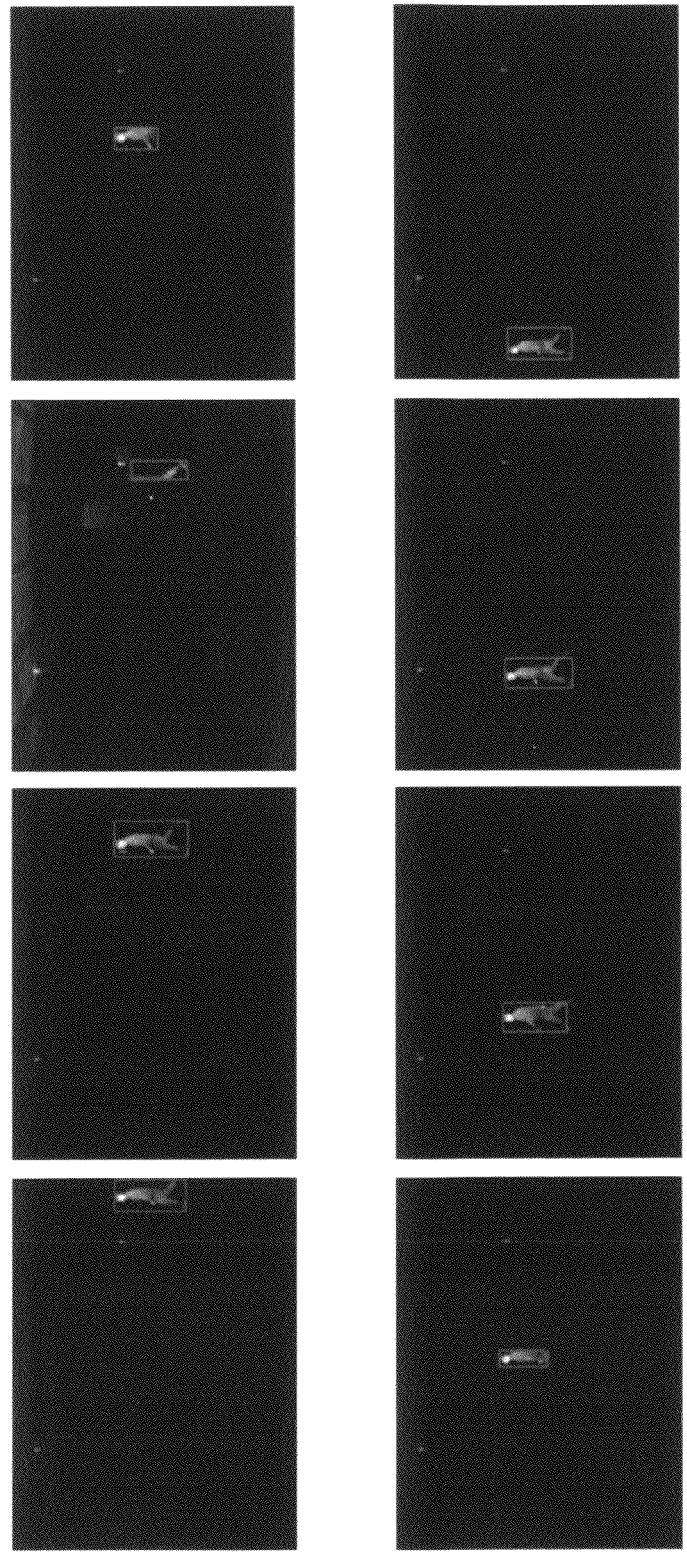
FIG. 8 is illustrative of the tracking capabilities of the present disclosure.
Figure 9A:
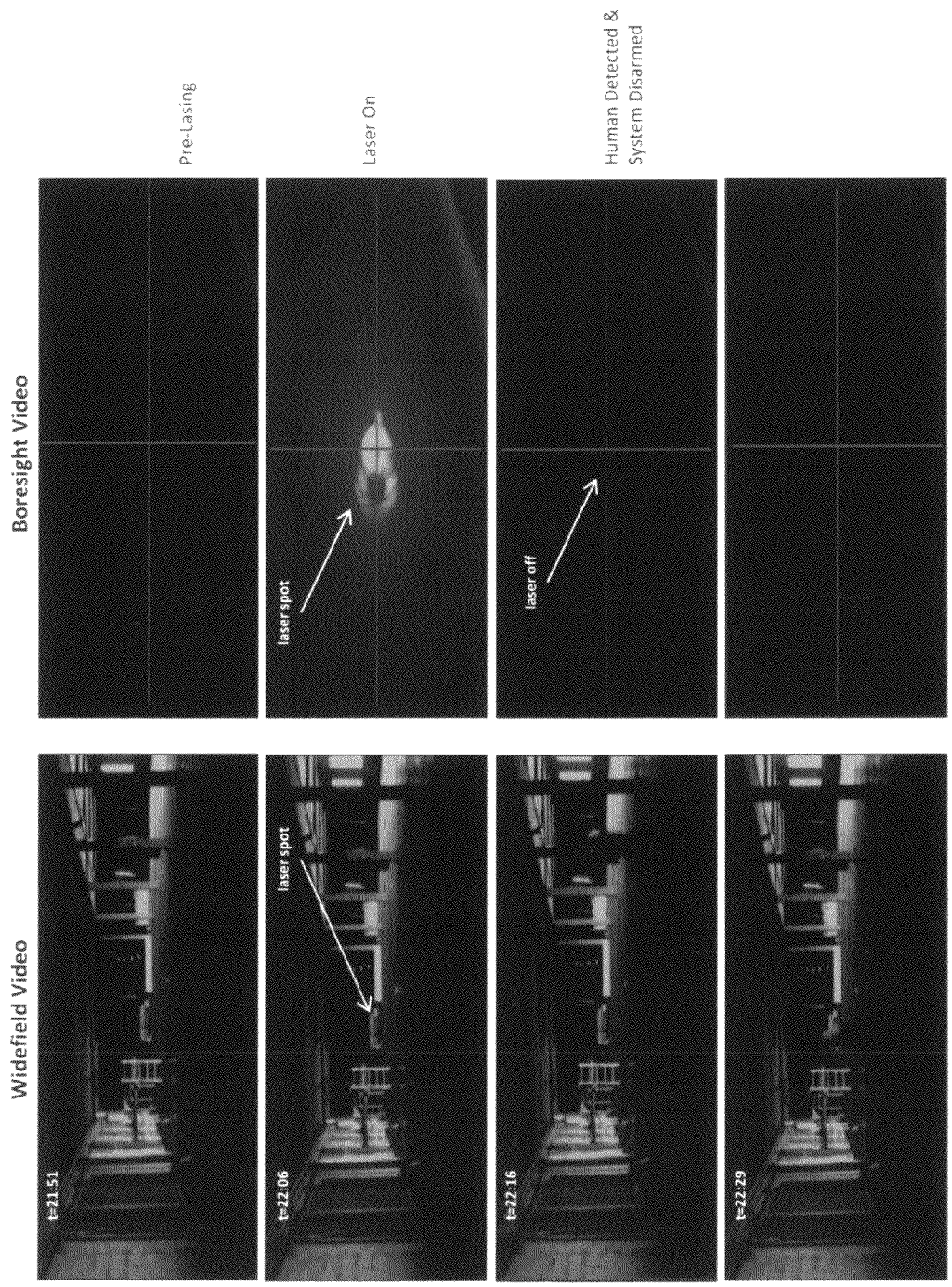
FIG. 9A is illustrative of the tracking capabilities of the present disclosure.
Figure 9B:
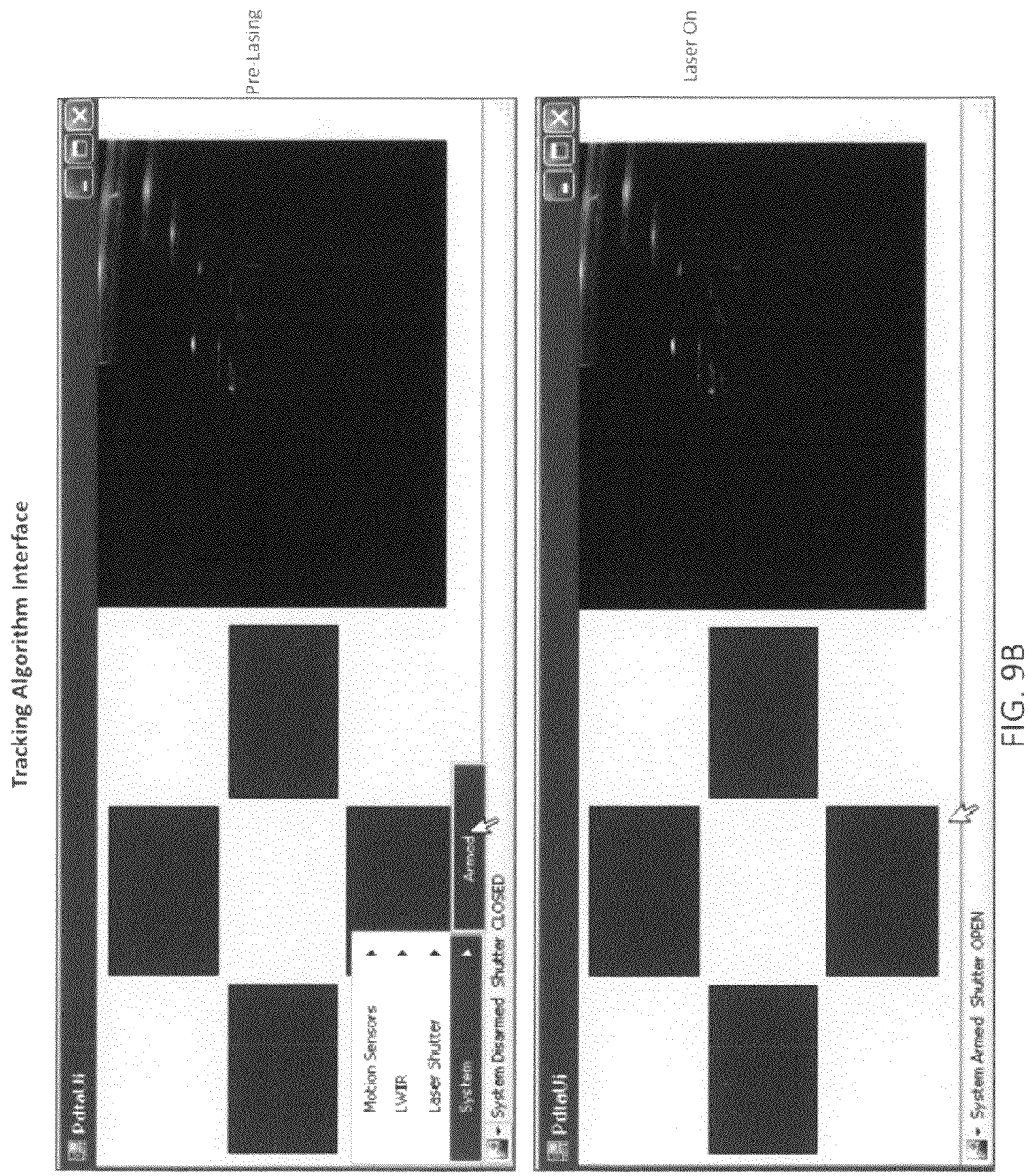
FIG. 9B is illustrative of the tracking capabilities of the present disclosure.
Figure 9C:
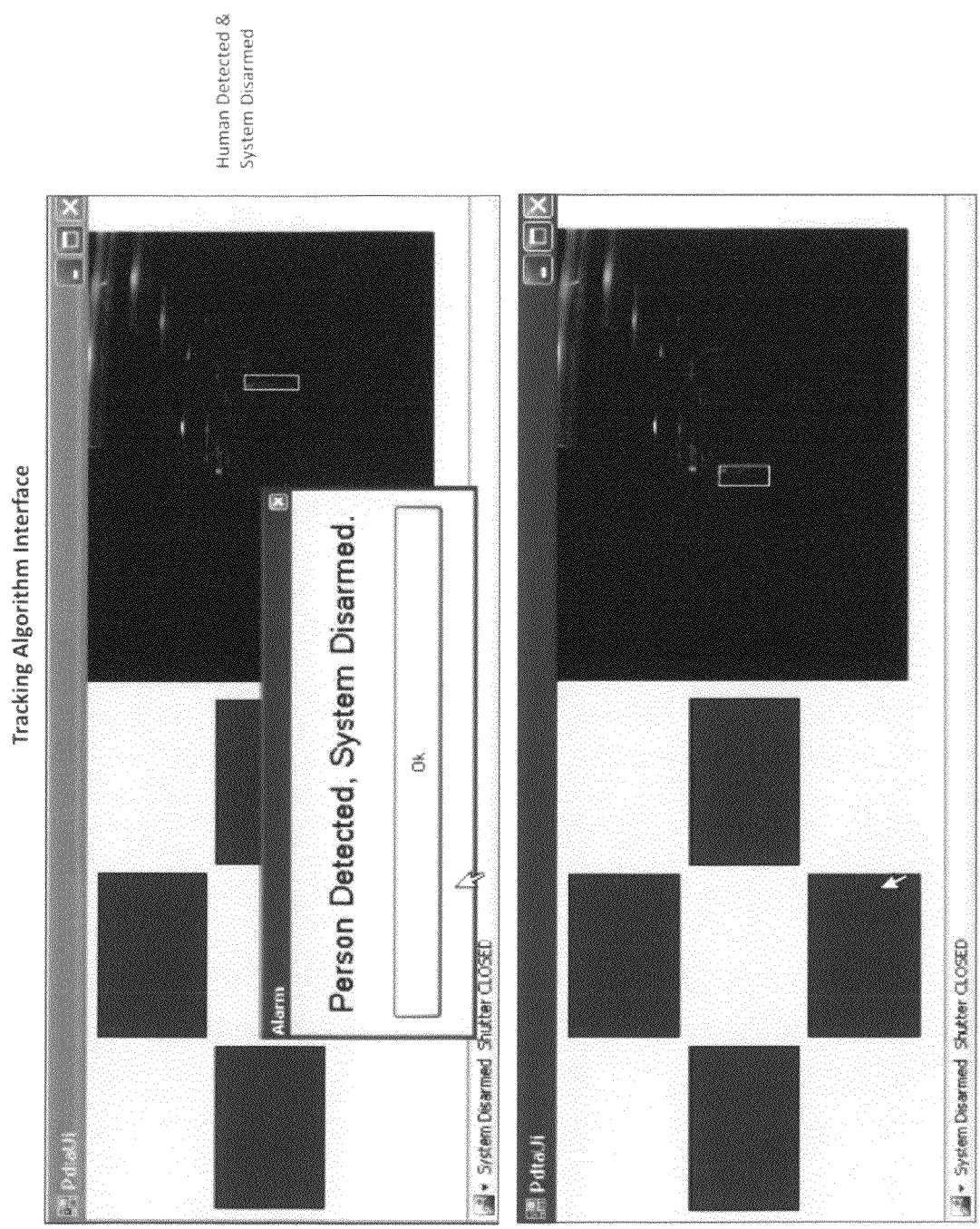
FIG. 9C is illustrative of the tracking capabilities of the present disclosure.

In one embodiment, the present disclosure provides for object tracking. A multi-target tracker based on a 6 state linear kalman filter may be used. This may be used to arbitrarily track a plurality of moving or stationary objects. Spatial and temporal features may be input into a Bayesian track classification algorithm. This is more fully described in relation to FIG. 8 herein.

In one embodiment, the present disclosure provides for Bayesian track classification. A Bayesian classifier may encode important features of the objects to be classified. In one embodiment, four classification features may be employed. Lookup tables may be generated in an offline training process. Two class estimates (i.e., "probability of a human" vs. "probability not a human") may be computed from lookup tables and from the features computed at runtime. If at least one track is declared to be class "human" in a single frame then the shutter may be closed.

Figure 7:
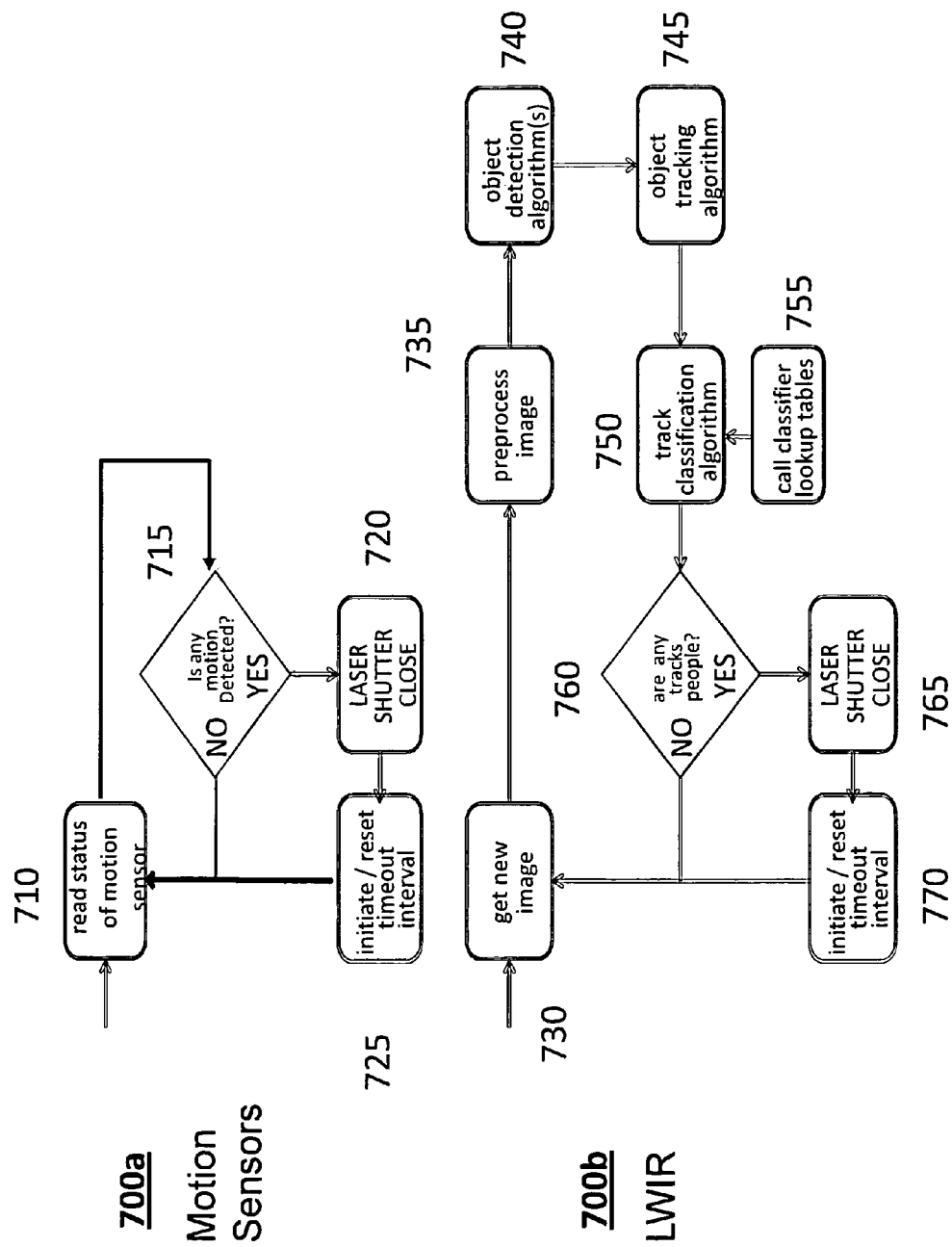
FIG. 7 is representative of a method of the present disclosure.

FIG. 7 illustrates two iterative methods that may be used for motion detection and/or object tracking. A method 700*a* may comprise the use of motion detectors. In such an embodiment, a method 700*a* may comprise reading the status of a motion sensor in step 710 and determining in step 715. If motion is detected, a laser shutter may be closed in step 720. If motion is not detected, initiation/resetting of a time out interval may be implemented in step 725.

In another embodiment, a method 700*b* may comprise the use of LWIR data. In one embodiment, the method 700*b* may comprise generating a new image in step 730. This image may be preprocessed in step 735 and an object detection algorithm implemented in step 740. An object tracking algorithm may be applied in step 745 and a track classification algorithm applied in step 750. Classifier lookup tables may be consulted in step 755. If people are detected in step 760 then a laser shutter may be closed in step 765. A timeout interval may be initiated/resent in step 770.

FIGS. 8 and 9A-9C are illustrative of human detection capabilities of the present discourse using LWIR data. As can be seen from these figures, a human can be detected and a system disarmed based on this presence.

Referring again to FIG. 6, if no human presence is detected, then an unknown target may be identified in step 630. In one embodiment, this identifying may comprising illuminating a region of interest to thereby generate a plurality of interacted photons. These interacted photons may be collected to thereby generate at least one Raman data set representative of said region of interest. In one embodiment, said Raman data set comprises at least one of: a Raman spectrum, a spatially accurate wavelength resolved Raman image, and combinations thereof. In one embodiment, said Raman data set may comprise a hyperspectral Raman image. This Raman data set may be analyzed to thereby identify said unknown target.

In one embodiment, the method 600 may further comprise passing a plurality of interacted photons through a FAST device operatively coupled to a spectrometer configured for generating a Raman data set. In another embodiment, a plurality of interacted photons may be passed through a filter. This filter may be selected from the group consisting of: a fixed filter, a dielectric filter, a tunable filter, and combinations thereof.

In one embodiment, the method 600 may further comprise obtaining and analyzing at least one LWIR data set substantially simultaneously with said illuminating of said region of interest to thereby determine at least one of: the presence of at least one human in said region of interest and no human presence in said region of interest. If at least one human is detected, the illumination may be stopped. This may be achieved by activating a laser shutter.

In one embodiment, a method 600 may further comprise providing a reference database comprising at least one reference data set, wherein each reference data set is associated with a known target. SWIR, LWIR, and/or Raman data sets obtained from interrogation of a sample scene, region of interest, and combinations thereof may be compared to at least one reference data set. This comparison may be used to identify regions of interest of a sample scene likely to comprise targets of interest or to identify unknown targets.

In one embodiment, this comparison may be achieved by applying one or more chemometric techniques. This chemometric technique may be selected from the group consisting of: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion, and combinations thereof.

In one embodiment, a method 600 may further comprise outputting a video image representative of a sample scene, a region of interest within said sample scene, and combinations thereof. This video image may be used to aid in surveillance and detection.

Figure 10A:
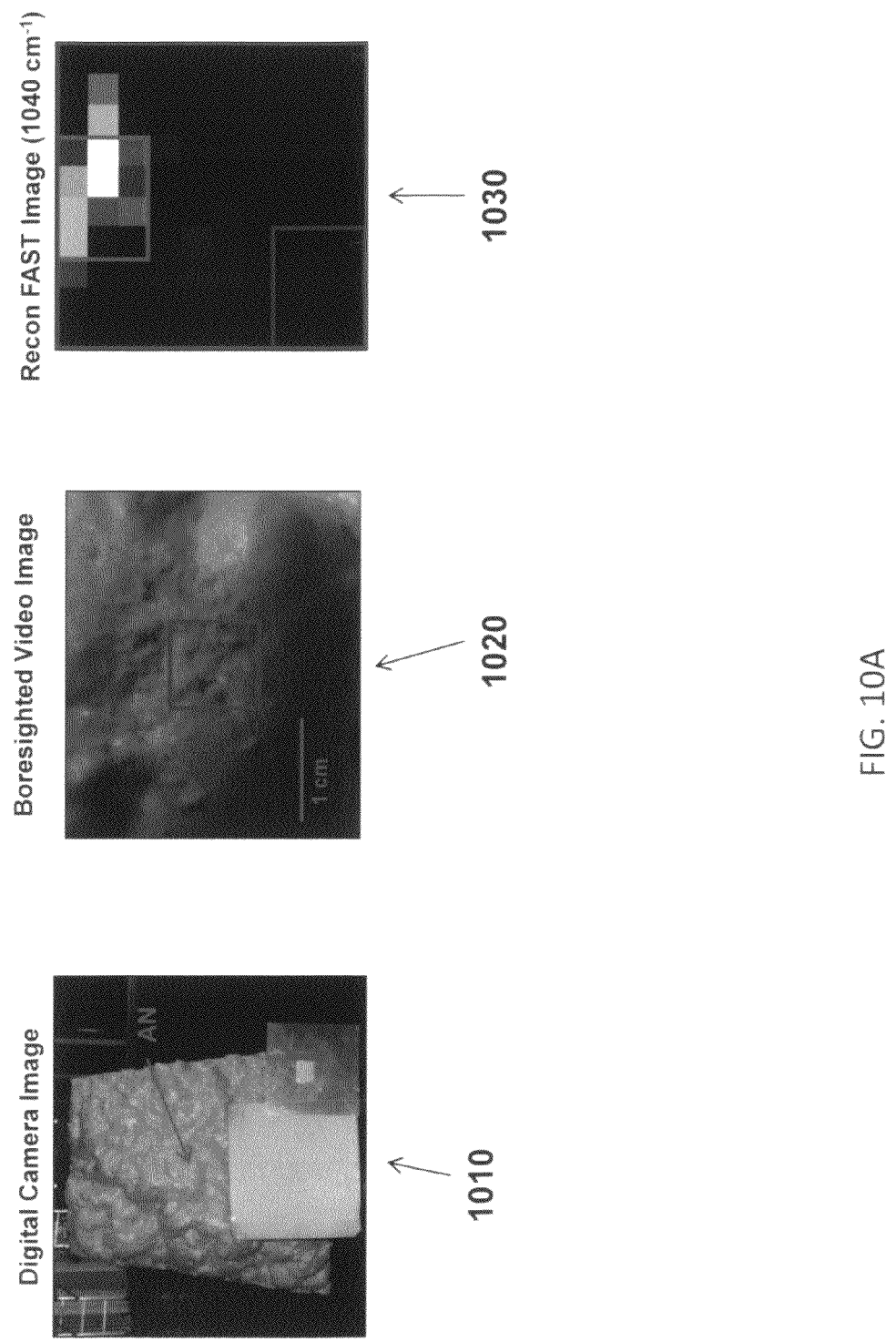
FIG. 10 A is representative of detection capabilities of the present disclosure.
FIG. 10B is representative of detection capabilities of the present disclosure.
Figure 10B:
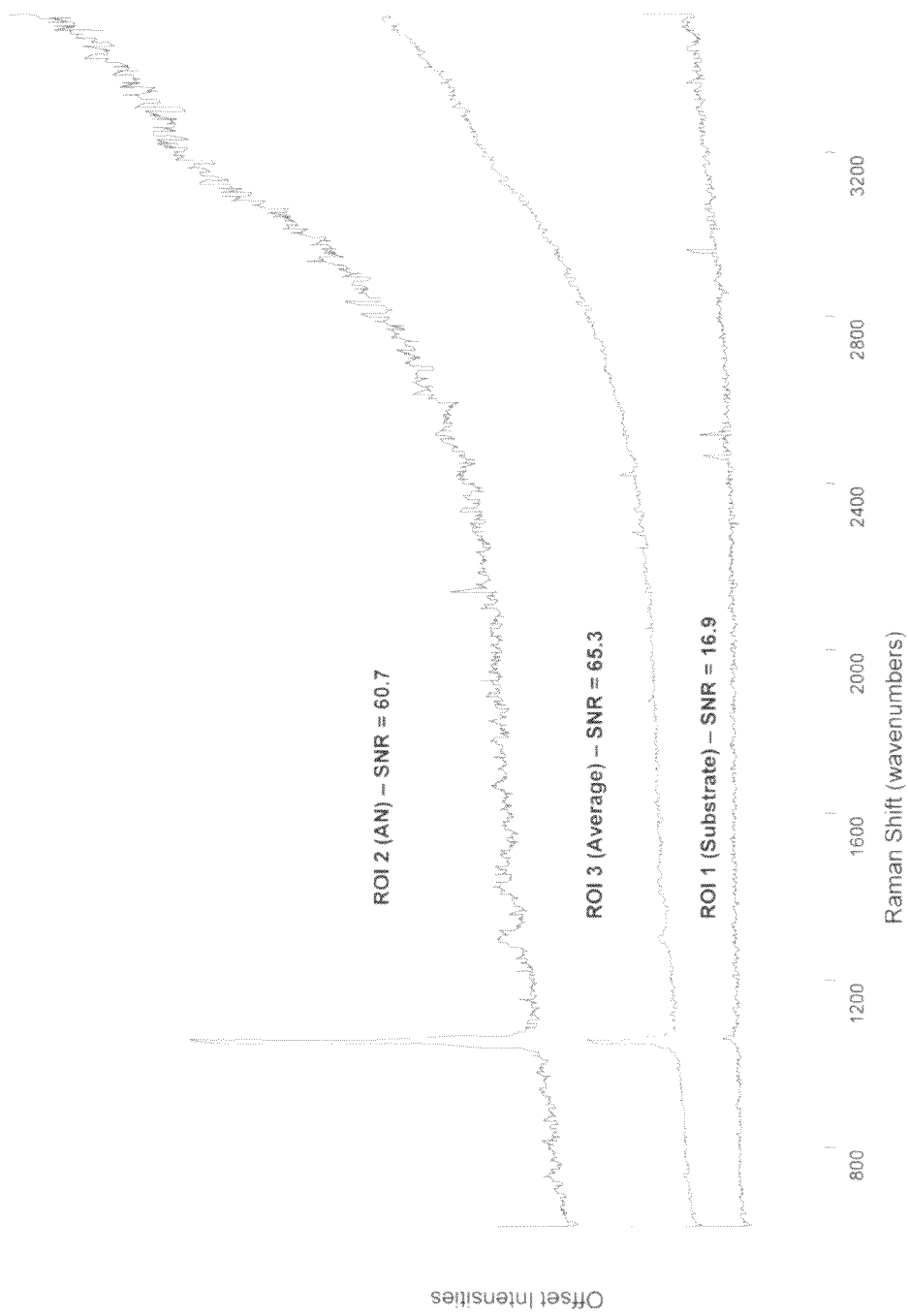

FIGS. 10A and 10B are illustrative of the detection capabilities of the present disclosure. FIGS. 10A and 10B illustrate the ability of the system and method disclosed herein to detect explosive material on a surface. A digital camera image 1010 illustrates a sample scene, 1020 represents a boresighted video image with a region of interest outlined in green. A FAST image is illustrated in 1030. Spectra associated with regions of interest in FIG. 10A are illustrated in FIG. 10B.

The present disclosure also provides for methods that may, in one or more embodiments, aid in targeting regions of interest using SWIR techniques. SWIR-ADA is an algorithm which may be configured for the autonomous real-time detection of unknown targets of interest. In one embodiment, it may operate on SWIR images as inputs. It departs from previous SWIR detection algorithms in multiple key ways discussed herein. In one embodiment, the method may comprise a video processing algorithm, which may incorporate temporal information in several stages. In one embodiment, detections may be tracked with a Kalman filter multi-target tracking algorithm across time intervals to validate via persistence. Image context may be incorporated extensively (i.e. the presence of shadows, edges, etc. is used to make detections more challenging or impossible for certain regions of the image) and every individual pixel gets its own detection threshold based on image context. Detection results are obtained from local image measures (local score image contrast and local image context for setting thresholds) and the method has a novel scale-invariant method for computing local contrast that holds potential for being highly effective for enhancing contrast in true targets and decreasing contrast for many false alarms ("multi-scale detection", a method which has received its own invention disclosure).

SWIR-ADA is agnostic to the source of "score" images used to capture chemical information (PLS regression images, two wavelength division images, entropy images, etc.). Multiple false alarm filters may be implemented to reduce false alarm rates while minimally reducing true positive detection rates. SWIR-ADA may be designed as a modular framework for the autonomous detection of objects of interest. As algorithm improvements are created (in score image generation, for example) these can be inserted into the SWIR-ADA processing chain with very little required in the way of code modification. Many of the processing steps in SWIR-ADA are designed to reduce the false alarm rate; as improved false alarm filters are created they can be incorporated into the false alarm filtering code.

Figure 11A:
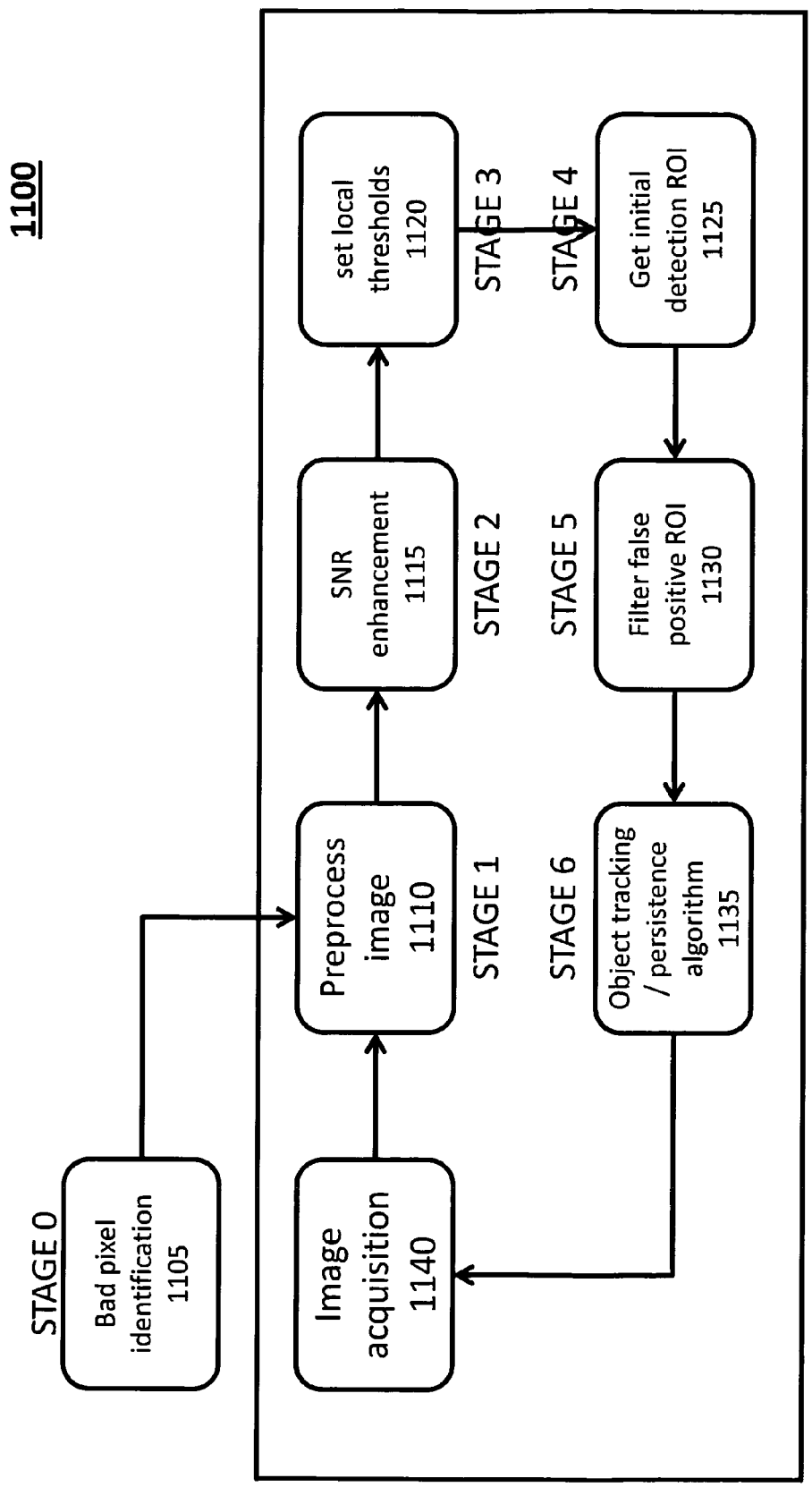
FIG. 11A is illustrative of a method of the present disclosure.

One embodiment of SWIR-ADA is illustrated by FIG. 11A. In on embodiment, a method 1100 may comprise identifying "bad" pixels in step 1105. This "bad" pixel identification may be used to identify those pixels in a camera or detector that do not function properly. In step 1110 preprocessing steps may be applied to at least one SWIR image generated by surveying a sample scene. This preprocessing may further comprise steps such as flatfielding, and detection of shadows and glares in an image. This preprocessing may provide an indication of pixels that can or cannot be trusted as providing accurate detection.

Step 1115 may provide for SNR enhancement. In one embodiment, step 1115 may further comprise imaging processing techniques to enhance local contrast within a data set. These methods may be referred to herein as Multi-Resolution Contrast Enhancement (MCRE) techniques.

A MRCE method as contemplated herein may be used to selectively adjust image contrast based on local signal intensities. Regions of a data set with low global contrast and "calm" local neighborhoods can be transformed into highly distinct regions of interest. In one embodiment, MRCE may pass a series of "kernels" of varying resolutions over every pixel of an image. Each kernel has a void "donut" region at the center that excludes the local neighborhood of the pixel under test. Local statistics may be computed for the pixels within the kernel that are not in the "donut" region. Multiple kernels at different scales must be used because it is never known ahead of time how big the true positive regions of interest are. The net result of this filter is that regions of interest that are faint globally can become very distinct when examined at a local resolution setting. This often enables significant SNR (signal to noise ratio) enhancement.

The method for computing MRCE is a novel application of an integral image formalism which allows for constant time computation of local image statistics. A common image processing application is to apply moving windows to all pixels in an image. Larger kernels require significantly more computation than small windows. With the integral image formalism tailored to the MRCE kernels, however, the same amount of time is required for all kernel sizes to compute the filter response over an entire image.

Figure 11B:
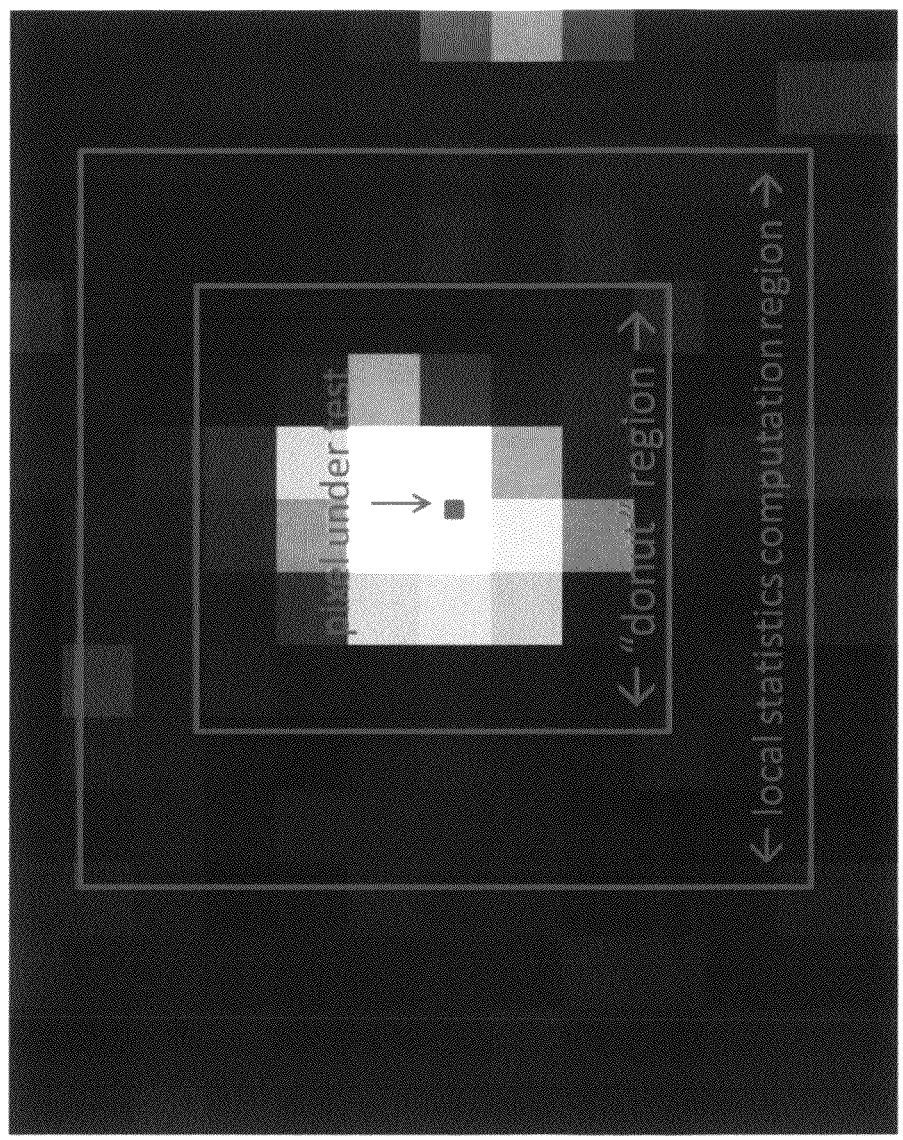
FIG. 11B is representative of a computation window of a method of the present disclosure.
Figure 11C:
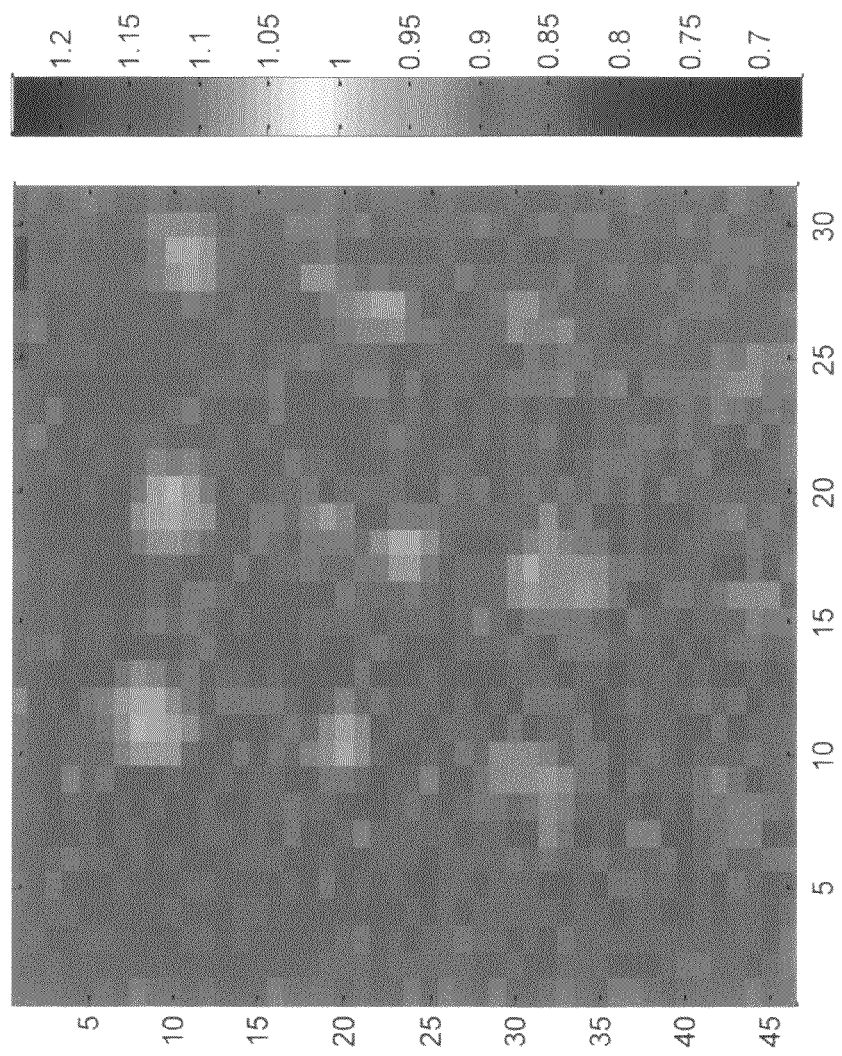
FIGS. 11C-11F are illustrative of the detection capabilities of the present disclosure.

FIG. 11B illustrates the basic computation window of the MCRE method. FIG. 11C contains a zoomed in false color "score image" with ammonium nitrate (AN) deposits, a typical explosive precursor material. The AN deposits are the yellow clusters arranged in a 4×3 grid on a car door. The score image was used in previous detection algorithms as the basis of whether or not a given cluster of pixels contained true positives. The AN regions have peak score image intensities of about 0.98, compared to about 0.9 for the local background. This is not a very significant difference (approximately $\frac{1}{11}$ greater than the local background) and automatically thresholding these intensities is not a trivial task.

Figure 11D:
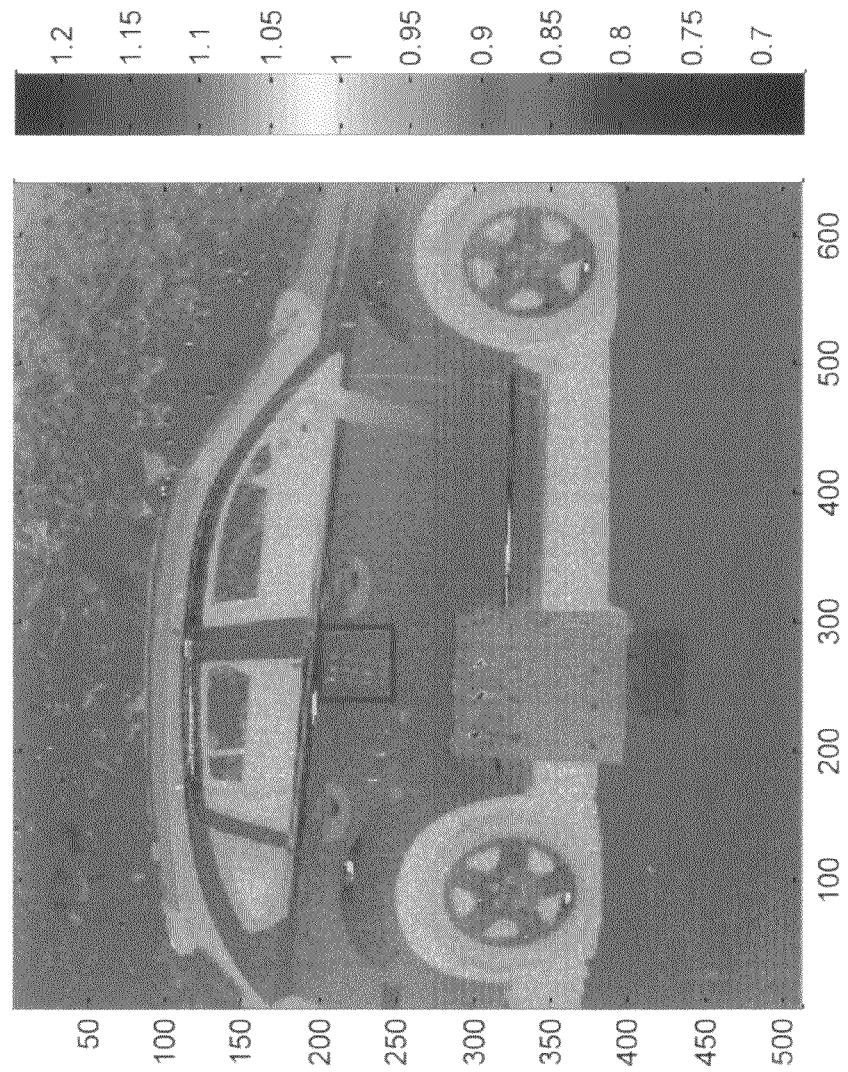

A more challenging matter is that globally the intensity value of the AN deposits is less than many other regions of the image. In FIG. 11D the zoomed out car coated with AN can be observed. The red box encloses the zoomed in region of FIG. 11C. The score image intensity for AN is less than the intensity of the car windows, tires, and many rocks in the background. Detecting AN without detecting any false positives is extremely problematic.

A more challenging matter still is that the score image intensity varies significantly depending on external conditions (sunlight, angle of illumination, etc.). The score value of 0.98 for the AN deposits in FIG. 11C could be significantly different if the data were acquired at a different time of day, if clouds were present, etc. This presents significant difficulty to creating a robust autonomous detection algorithm.

Figure 11E:
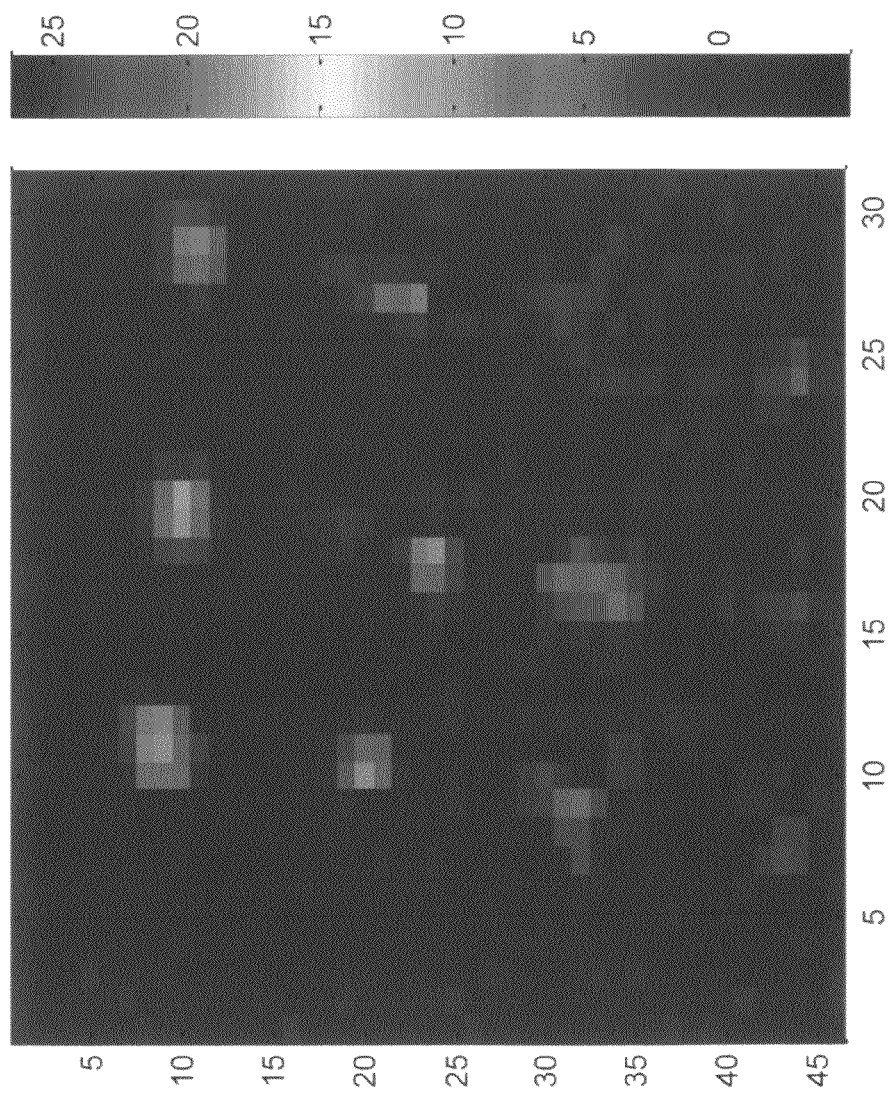

The MRCE method aims to overcome these challenges to autonomous detection by expressing score image intensities in terms of the local intensity statistics. The "score image" is transformed into the "SNR image" as output of the MRCE algorithm. The value of each pixel in the SNR image represents the highest computed local SNR value for all resolutions evaluated. The output of the MRCE algorithm is demonstrated in FIG. 11E. The peak score image intensity was 0.98, compared to a background of 0.9. In the resultant SNR image peak SNR is transformed to 11 and the background intensities are roughly 0 (even negative). This results in a significant gain in image contrast. The task of thresholding the image is thus much easier and more robust to changes in external conditions.

Figure 11F:
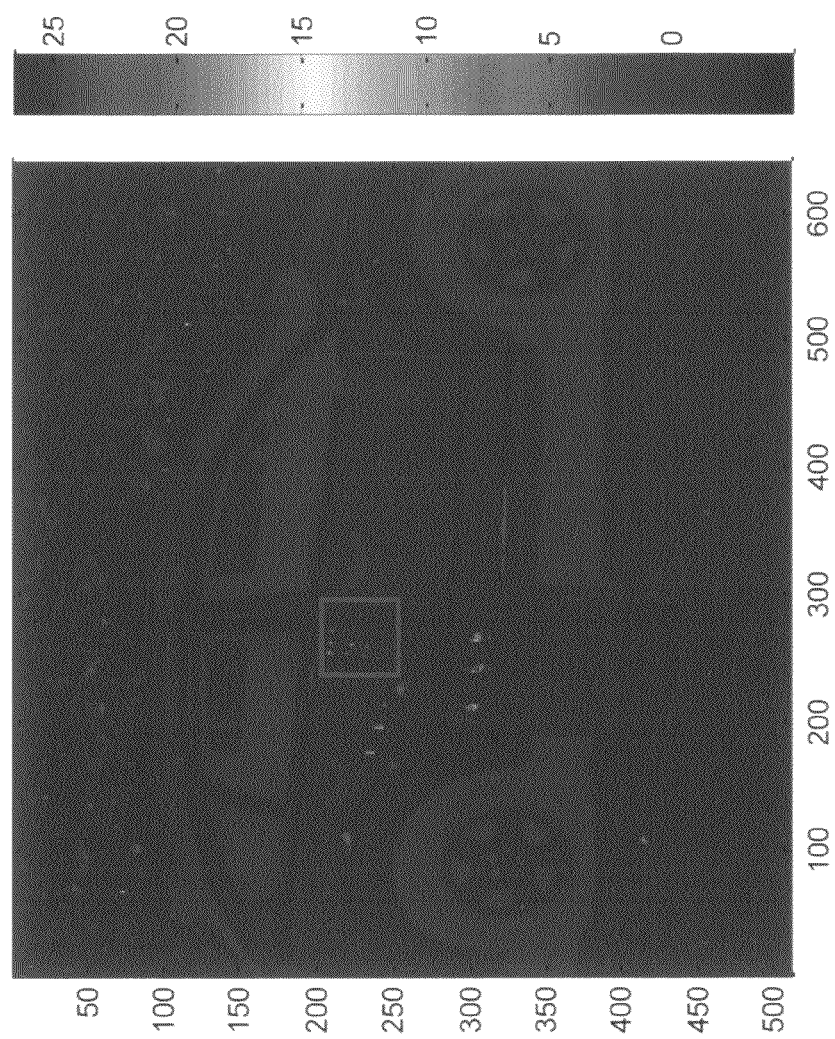

The MRCE algorithm also results in significant image flattening for true positive regions of an image. Recall from 11 D that in the score image the AN deposits often have a lower intensity than large sections of the background (i.e. the car windows). After processing by the MRCE algorithm, however, the windows have SNR <2 (see FIG. 5). True positive ROIs are now more than 5× as intense as the windows instead of being dimmer. The red box in FIG. 11F contains the high zoom region of FIG. 11E. Note that post-MRCE the AN deposits are very distinct. Compare this to the very faint contrast apparent in the same region of the score image in FIG. 11D.

Referring again to FIG. 11A, in step 1120 local thresholds may be set. In step 1125 initial regions of interest may be detected. Step 1125 may comprise the generation of a binary image indicative of material identity. "Spots" in a binary image may be indicative of regions of interest.

False positives may be filtered in step 1130. In one embodiment, this filtering may be achieved by applying one or more tests which may account for morphological and/or geometrical characteristics of regions of interest and/or unknown targets within regions of interest.

In step 1135 one or more object tracking/persistence algorithms may be applied. In one embodiment, methodologies referred to as real-time track-based persistence methods may be implemented. Persistence methods utilize temporal data to predict where regions of interest should be in each successive image frame. In one embodiment, a first image frame may be used to predict where a region of interest should appear in a next successive image frame. This second image frame may then be used to confirm the location of a region of interest.

In detecting objects of chemical interest in SWIR (shortwave infrared) imagery the signal to noise ratio (SNR) is often low. To enable detections a threshold must be set low with respect to ambient noise levels. As a result many typical objects of interest can only be detected along with many false positives. In practice the use of temporal persistence requirements have been demonstrated to significantly reduce false alarm rates. Temporal persistence amounts to segmenting an image into regions of interest (ROIs) and counting how often these ROIs are detected. In one embodiment, a minimum "M out of N" detection criteria is established (i.e., a given ROI must be detected in at least 3 out of the last 5 frames to be declared persistent).

Novel features of persistence as contemplated herein center on using an object tracking algorithm as the vehicle for applying temporal persistence requirements. The tracking algorithm can be of any form (Kalman filter, least squares, particle filter, etc.). Object trackers have a number of qualities that make them a suitable technique for applying persistence to dynamic, real-time scenarios. They are inherently developed for following around moving objects, but they also extend to cases where the object of interest is stationary. Trackers are also very real-time friendly. Another benefit of trackers that the direct counting persistence cannot provide is the ability to provide feedback into the detection process. The ROI tracking algorithm in SWIR-ADA is used to provide feedback ("track before detect") to locally reduce detection thresholds where tracked objects are anticipated to be.

Figure 11G:
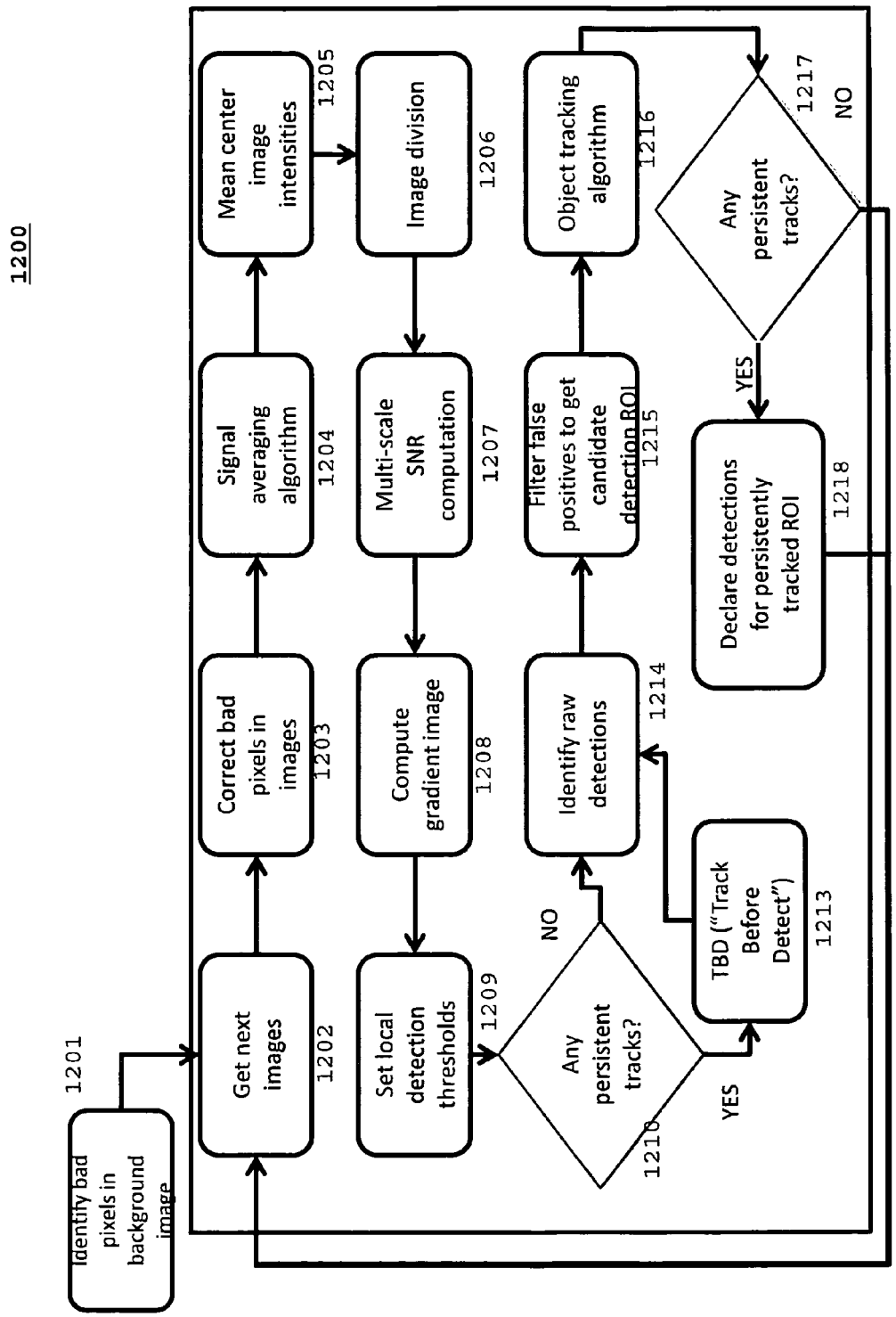

FIG. 11G is a more detailed depiction of a SWIR-ADA methodology. In step 1201 "bad" pixels may be identified in a background image. In step 1202 next images may be obtained. "Bad" pixels may be corrected in images in step 1203. In step 1204 a signal averaging algorithm may be applied. In step 1205 the mean of image intensities may be ascertained. Image division may occur in step 1206. In step 1207 multi-scale SNR computation may be performed and in step 1208 a gradient image may be computed. In step 1209 a local detection threshold may be applied. In step 1210 whether or not any persistent tracks were detected may be ascertained. If no persistent tracks were detected in step 1210 then raw detections may be identified in step 1214. In step 1215 false positives may be filtered to get candidate detection regions of interest. One or more object tracking methods may be applied in 1216 and persistence of tracks determined in step 1217. Detections for persistently tracked regions of interest can be declared in step 1218. If persistent tracks are determined in step 1210, the additional "track before detect" step may be applied in step 1213.

Figure 12B:
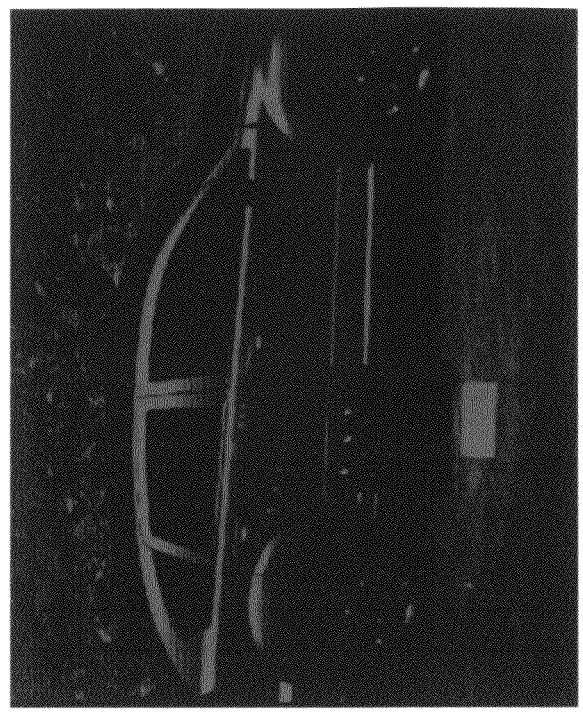
FIGS. 12A-12C are illustrative of the detection capabilities of the present disclosure.
Figure 12A:
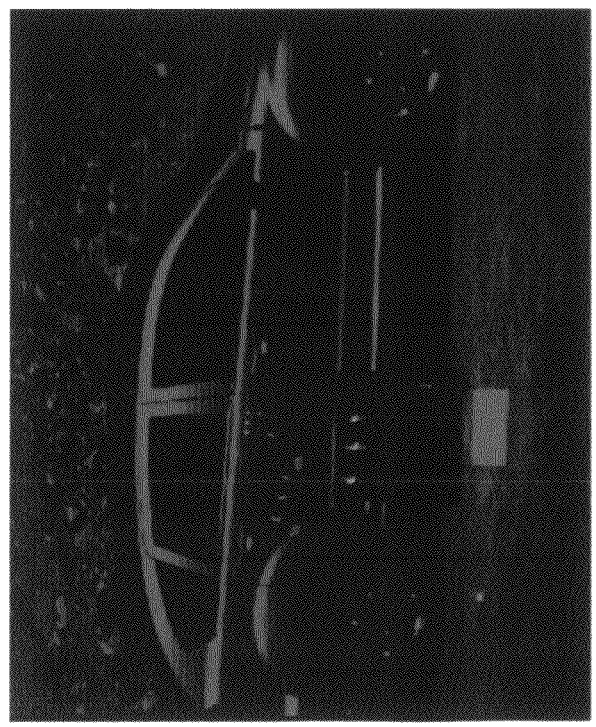
Figure 12C:
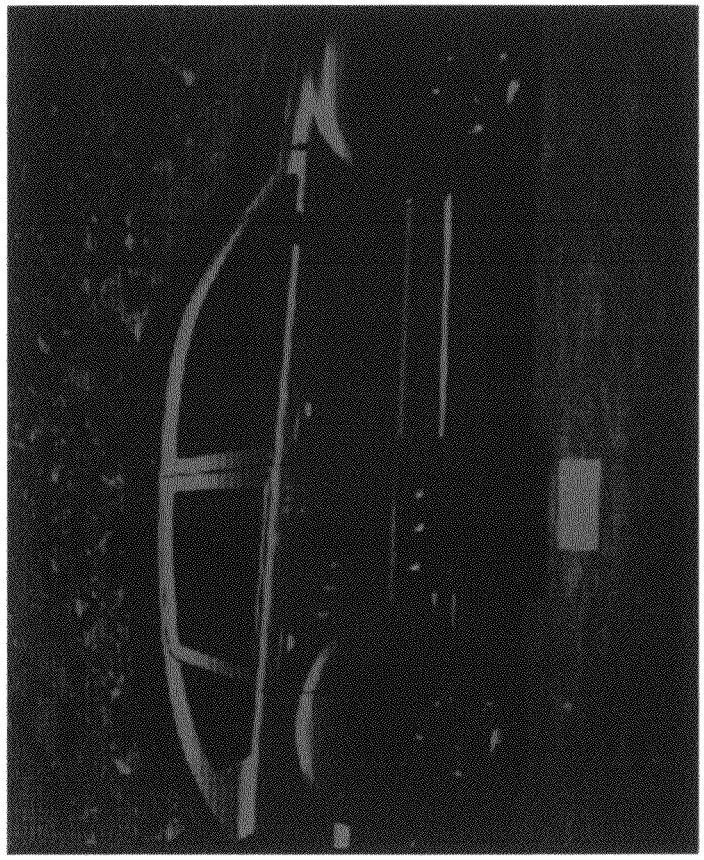

The concept outlined in FIGS. 11A and 11G are more fully demonstrated in FIGS. 12A-C. In these images a car has been painted with explosives precursors and is being analyzed with the LightGuard sensor at several different wavelengths. Green pixels indicate the presence of non-persistent detections. Red pixels represent the location of persistently tracked ROI. In FIG. 12A, the first image of the video sequence, there are many non-persistent detections of both true and false positives. Note that since it is the first frame of the sequence there can be no persistent detections. FIG. 12B shows the $6^{th}$ frame of the video sequence, and FIG. 12C shows the $9^{th}$ frame. Application of the real-time persistence algorithm allows for true positives to be detected persistently without the detection of any false positives.

The present disclosure may be embodied in other specific forms without departing from the spirit or essential attributes of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method comprising:
    targeting at least one region of interest in a sample scene comprising at least one unknown target by
        generating at least one SWIR data set representative of the sample scene, and
        analyzing the at least one SWIR data set to identify the region of interest;
    surveying the region of interest to determine one or more of human presence in the region of interest and no human presence in the region of interest, wherein if no human presence is detected, the method further comprises identifying the unknown target by
        illuminating the region of interest to generate a plurality of interacted photons;
        assessing the plurality of interacted photons to generate at least one Raman data set of the interacted photons; and
        analyzing the at least one Raman data set to identify the unknown target.

2. The method of claim 1, wherein the surveying further comprises
    generating at least one LWIR data set representative of one or more of the sample scene, the region of interest, and combinations thereof; and
    analyzing the at least one LWIR data set to determine one or more of human presence in the region of interest and no human presence in the region of interest.

3. The method of claim 1, wherein the surveying further comprises sensing for motion to determine one or more of human presence in the region of interest and no human presence in the region of interest.

4. The method of claim 1 further comprising:
    illuminating the region of interest to generate a plurality of interacted photons of the region of interest;
    generating at least one LWIR data set from the plurality of interacted photons; and
    analyzing the at least one LWIR data set to determine one or more of human presence in the region of interest and no human presence in the region of interest, and if at least one human presence is detected in the region of interest, ceasing the illuminating, wherein the illuminating, generating and analyzing are performed substantially simultaneously.

5. The method of claim 1, further comprising passing the plurality of interacted photons through a fiber array spectral translator device.

6. The method of claim 1, further comprising providing at least one Raman reference database comprising at least one Raman reference data set, wherein each Raman reference data set corresponds to at least one known target.

7. The method of claim 1, wherein analyzing the at least one SWIR data set further comprises comparing the at least one SWIR data set to at least one reference data set.

8. The method of claim 6, wherein analyzing the Raman data set further comprises comparing the at least one Raman data set to at least one reference Raman data set.

9. The method of claim 1, further comprising filtering the plurality of interacted photons.

10. The method of claim 1, wherein the at least one SWIR data set comprises one or more of a SWIR spectrum, a spatially accurate wavelength resolved SWIR image, and combinations thereof.

11. The method of claim 1, wherein the at least one SWIR data set comprises a hyperspectral SWIR image.

12. The method of claim 2, wherein the at least one LWIR data set comprises one or more of a LWIR spectrum, a LWIR image, and combinations thereof.

13. The method of claim 2, wherein the at least one LWIR data set comprises a hyperspectral LWIR image.

14. The method of claim 1, wherein the at least one Raman data set comprises one or more of a Raman spectrum, a spatially accurate wavelength resolved Raman image, and combinations thereof.

15. The method of claim 1, wherein the at least one Raman data set comprises a Raman hyperspectral image.

16. The method of claim 1, wherein the surveying further comprises applying one or more of an object detection algorithm, an object tracking algorithm, and combinations thereof.

17. The method of claim 1, further comprising outputting a video image of one or more of the sample scene, the region of interest, and combinations thereof.

18. A non-transitory storage medium containing machine readable program code, which, when executed by a processor, causes the processor to perform the following:
   identify a sample scene by causing a first detector to generate at least one SWIR data set representative of the sample scene, and
   analyze the at least one SWIR data set to identify a region of interest within the sample scene, wherein the region of interest comprises an unknown target;
   survey the region of interest to determine one or more of human presence in the region of interest and no human presence in the region of interest, wherein if no human presence is detected,
   identify the unknown target by
   illuminating the region of interest to generate a plurality of interacted photons;
   causing a second detector to generate at least one Raman data set of the unknown target; and
   analyzing the Raman data set to identify the unknown target.

19. The non-transitory storage medium of claim 18 which when executed by a processor further causes the processor to survey the region of interest by causing a third detector to generate at least one LWIR data set of one or more of the sample scene, the region of interest, and combinations thereof.

20. The non-transitory storage medium of claim 19, which, when executed by a processor, further causes the processor compare one or more of the at least one SWIR data set, at least one LWIR data set, and at least one Raman data set to at least one reference data set in a reference database, wherein each reference data set is associated with a known target.

21. The non-transitory storage medium of claim 19, which, when executed by a processor, further causes the processor to communicate with at least one motion sensor to assess movement in one or more of a sample scene, a region of interest, and combinations thereof.

22. The non-transitory storage medium of claim 19, which, when executed by a processor, further causes the processor to obtain and analyze at least one LWIR data set substantially simultaneously while causing an illumination source to illuminate the region of interest to determine one or more of the presence of at least one human in the region of interest and no human presence in the region of interest, and if at least one human is detected in the region of interest, cause the illumination source to cease illuminating.

* * * * *